US010568827B2

(12) United States Patent
Miyake et al.

(10) Patent No.: US 10,568,827 B2
(45) Date of Patent: Feb. 25, 2020

(54) EXTERNAL DERMAL AGENT FOR REDUCING YELLOWISH DULLNESS

(71) Applicant: Hayashibara Co., Ltd., Okayama-shi, Okayama (JP)

(72) Inventors: Masaki Miyake, Okayama (JP); Motoyuki Suzuki, Okayama (JP); Tatsuya Ishihara, Okayama (JP); Toshio Ariyasu, Okayama (JP)

(73) Assignee: HAYASHIBARA CO., LTD., Okayama (JP)

(*) Notice: Subject to any disclaimer, the term of this patent is extended or adjusted under 35 U.S.C. 154(b) by 0 days.

(21) Appl. No.: 15/756,698

(22) PCT Filed: Sep. 1, 2016

(86) PCT No.: PCT/JP2016/075718
§ 371 (c)(1),
(2) Date: Mar. 1, 2018

(87) PCT Pub. No.: WO2017/038951
PCT Pub. Date: Mar. 9, 2017

(65) Prior Publication Data
US 2018/0243195 A1 Aug. 30, 2018

(30) Foreign Application Priority Data
Sep. 2, 2015 (JP) .................. 2015-173358

(51) Int. Cl.
*A61K 8/60* (2006.01)
*A61K 8/36* (2006.01)
*A61K 8/365* (2006.01)
*A61K 8/368* (2006.01)
*A61K 8/49* (2006.01)
*A61K 31/7048* (2006.01)
*A61K 9/20* (2006.01)
*A61K 31/198* (2006.01)
*A61Q 19/00* (2006.01)
*A61K 9/16* (2006.01)
*A61K 31/702* (2006.01)
*A61K 9/08* (2006.01)
*A61K 31/353* (2006.01)
*A61K 31/19* (2006.01)
*A61Q 19/02* (2006.01)

(52) U.S. Cl.
CPC .............. *A61K 8/602* (2013.01); *A61K 8/36* (2013.01); *A61K 8/365* (2013.01); *A61K 8/368* (2013.01); *A61K 8/49* (2013.01); *A61K 8/498* (2013.01); *A61K 8/60* (2013.01); *A61K 9/08* (2013.01); *A61K 9/16* (2013.01); *A61K 9/20* (2013.01); *A61K 31/19* (2013.01); *A61K 31/198* (2013.01); *A61K 31/353* (2013.01); *A61K 31/702* (2013.01); *A61K 31/7048* (2013.01); *A61Q 19/00* (2013.01); *A61Q 19/02* (2013.01)

(58) Field of Classification Search
CPC ........ A61K 8/602; A61K 8/498; A61K 8/368; A61K 8/365; A61K 8/36; A61Q 19/02
USPC .......................................... 514/27
See application file for complete search history.

(56) References Cited

U.S. PATENT DOCUMENTS

| 9,492,368 | B2* | 11/2016 | Ishihara | ............... | C07H 19/167 |
| 9,757,408 | B2* | 9/2017 | Kohno | ............... | A61K 31/7076 |
| 2006/0018861 | A1* | 1/2006 | Chen | ...................... | A61K 8/602 |
| | | | | | 424/70.14 |
| 2006/0018862 | A1 | 1/2006 | Chen et al. | | |
| 2013/0165399 | A1* | 6/2013 | Kohno | ............... | A61K 31/7076 |
| | | | | | 514/47 |

FOREIGN PATENT DOCUMENTS

| CN | 104224561 A | 12/2014 |
| JP | 7099498 A | 3/1998 |
| JP | 11346792 A | 12/1999 |
| JP | 2002255827 A | 9/2002 |
| JP | 2004352627 A | 12/2004 |
| JP | 2005289913 A | 10/2005 |
| JP | 2006273811 A | 10/2006 |
| JP | 2007254345 A | 10/2007 |
| JP | 20116462 A | 1/2011 |
| JP | 201231106 A | 2/2012 |
| WO | 2009116450 A | 9/2009 |
| WO | 2013018779 A1 | 2/2013 |
| WO | 2016027837 A1 | 2/2016 |

OTHER PUBLICATIONS

Hirao et al. Carbonylation of cornified envelopes in the stratum corneum. FEBS Letters 579 (2005) 6870-6874. (Year: 2005).*
Alpha Glucosyl Hesperidin | Products | Toyo Sugar Refining Co.,ltd. http://www.toyosugar.co.jp/en/item/hesperidin.html. Copyright © 2011. (Year: 2011).*
García-Salas et al. Influence of technological processes on phenolic compounds, organic acids, furanic derivatives, and antioxidant activity of whole-lemon powder. Food Chemistry 141 (2013) 869-878. (Year: 2013).*
Soto et al. Recovery, concentration and purification of phenolic compounds by adsorption: A review. Journal of Food Engineering 105 (2011) 1-27. (Year: 2011).*

* cited by examiner

*Primary Examiner* — Yih-Horng Shiao
(74) *Attorney, Agent, or Firm* — Browdy and Neimark, PLLC

(57) ABSTRACT

[Object] The present invention has an object to provide an external dermal agent for reducing skin yellowness already generated in the skin.
[Means to Attain the Object] The above object is solved by providing an external dermal agent for reducing skin yellowness already generated in the skin, which contains hesperetin and/or glycosyl hesperetin as an effective ingredient(s).

8 Claims, 4 Drawing Sheets

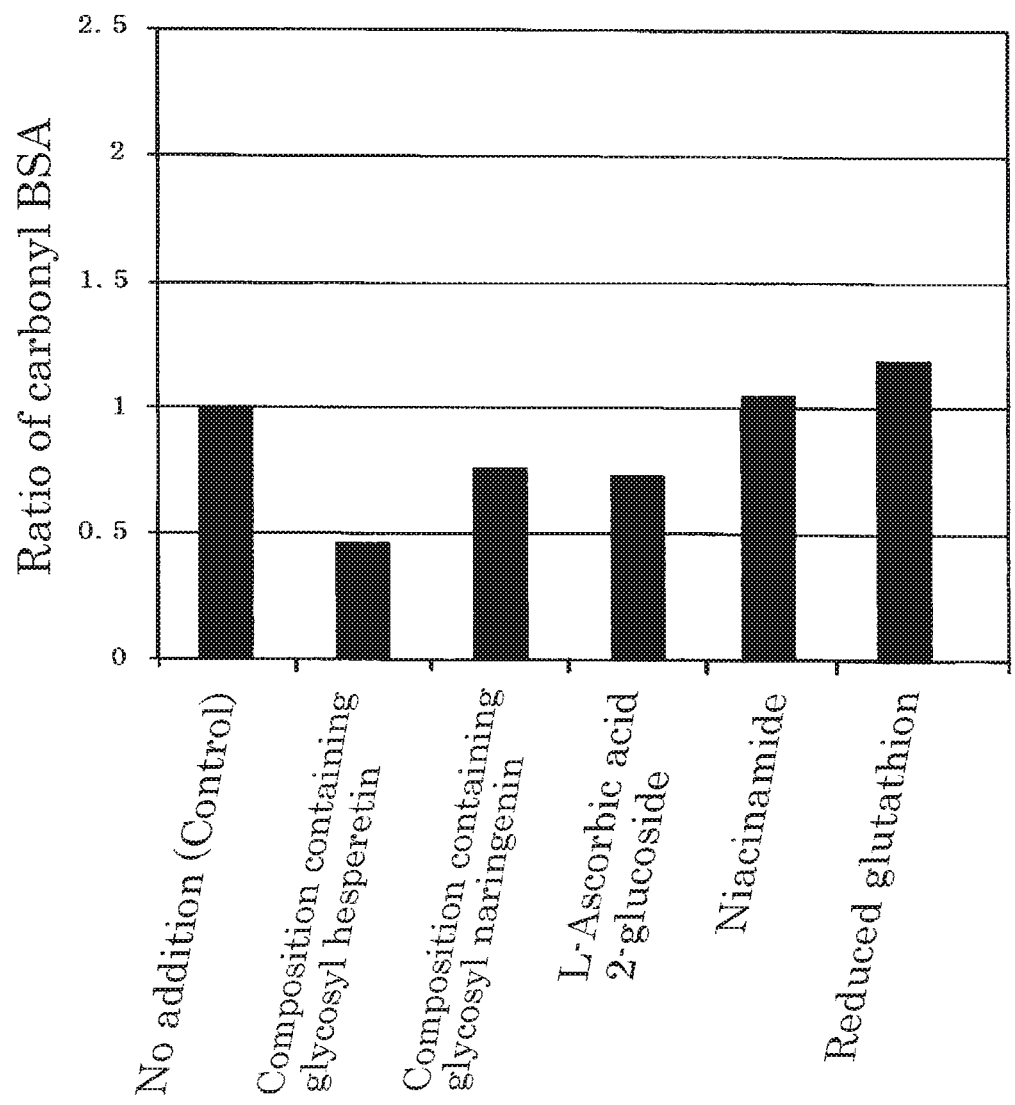
[FIG. 1]

[FIG. 2]
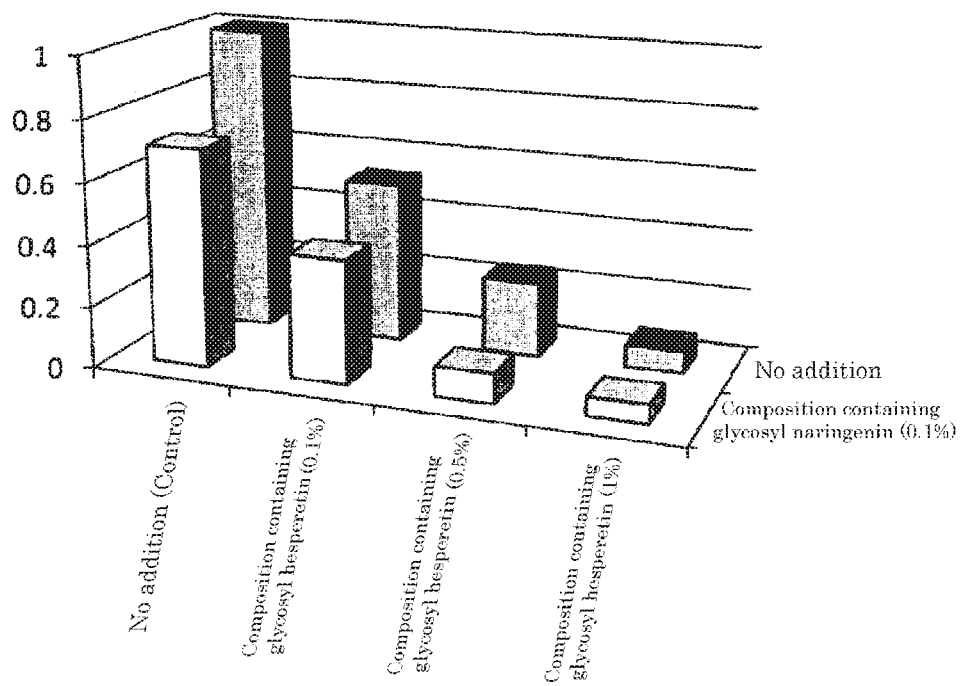
[FIG. 3]
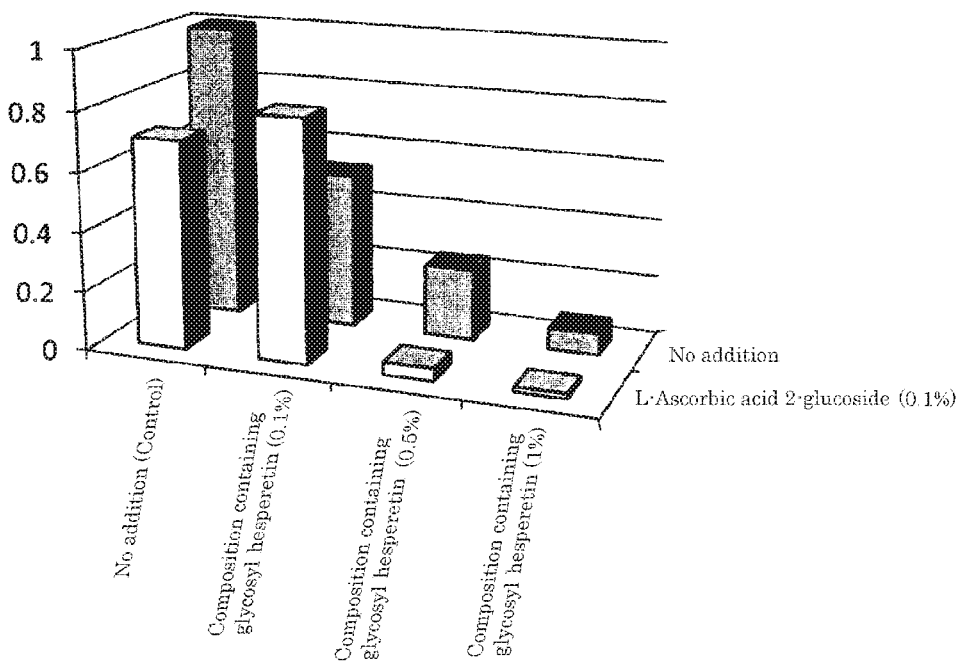

[FIG. 4]
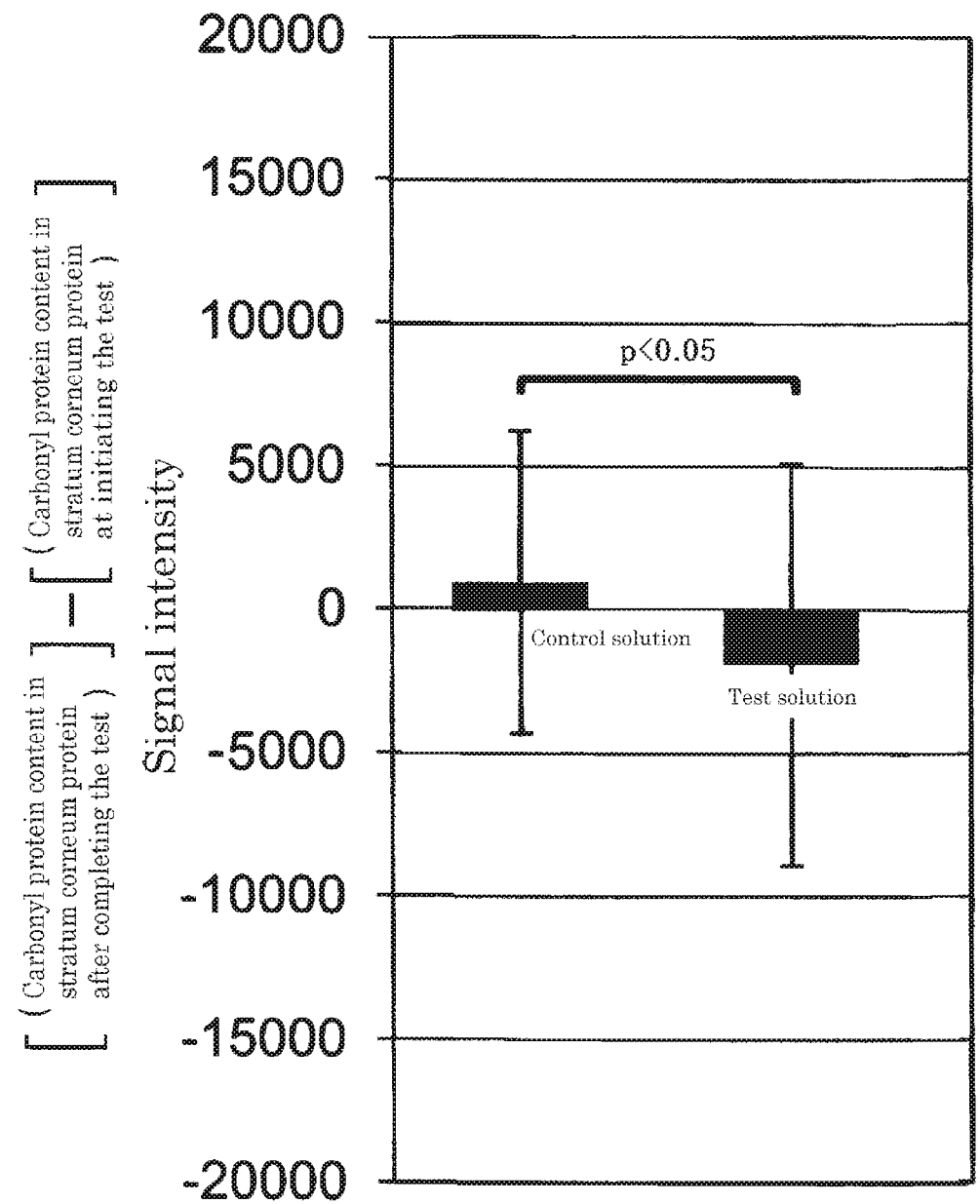

[FIG. 5]
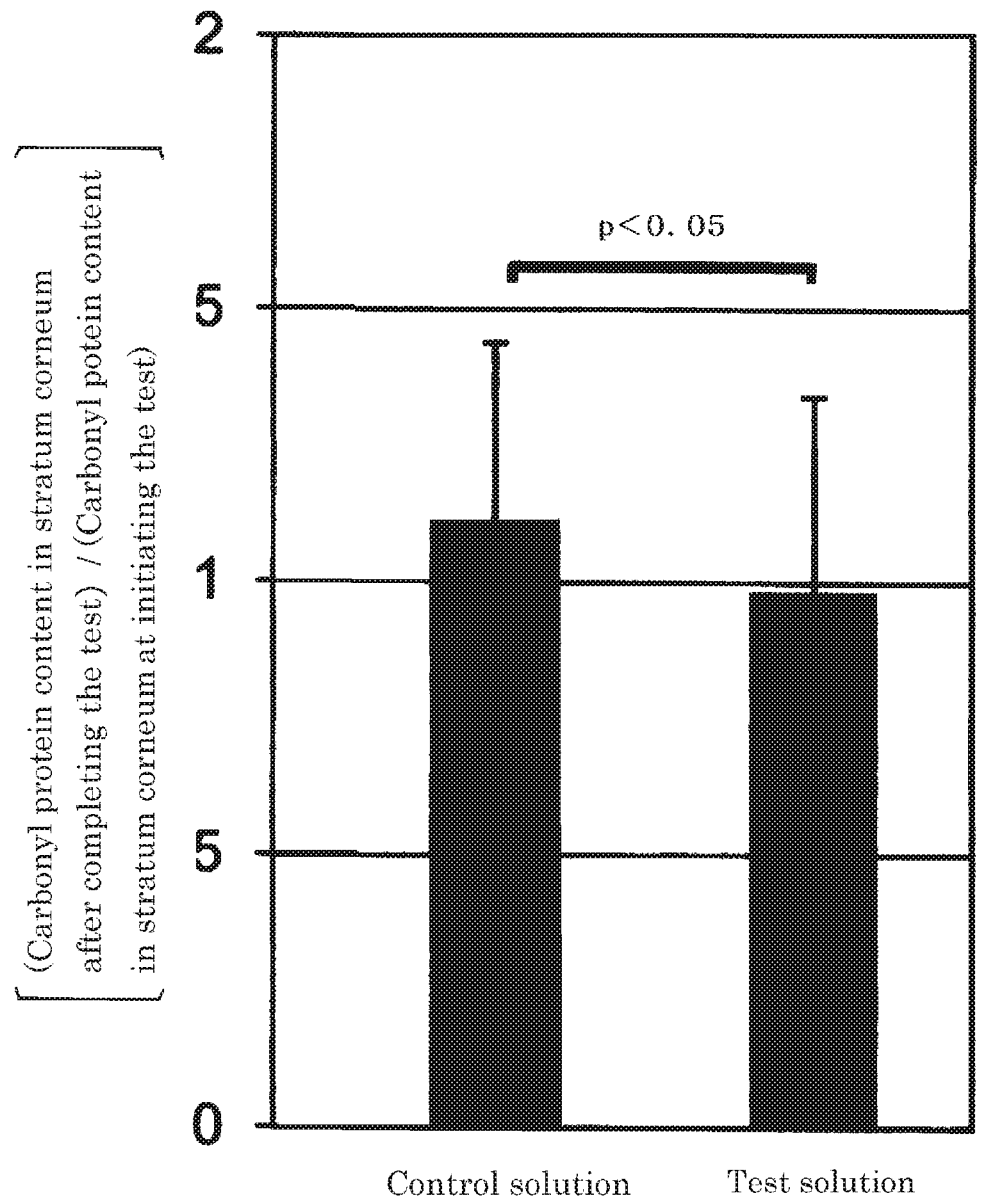

EXTERNAL DERMAL AGENT FOR REDUCING YELLOWISH DULLNESS

TECHNICAL FIELD

The present invention relates to an external dermal agent for reducing the already-generated yellowish dullness in the skin.

BACKGROUND

Yellowish dullness in the skin, meaning that the color tone of the skin becomes to show yellowness with ageing, is simply called "skin yellowness", hereinafter, unless specified otherwise, and it is considered problematic in the art in terms of skin care. It was once said that the denaturation of proteins in the skin was a major factor of inducing skin yellowness (i.e., saccharification or Maillard reaction); however, nowadays, it is said that the denaturation of proteins in the dermis, existing in a deeper part of the skin (i.e., carbonylation), would be such a major factor.

Since skin transparency may be deteriorated as the increase of skin yellowness and this may tend to make you look older than your actual age, measures against skin yellowness are distinctly important to keep your youthful appearance. As an actual example of such measures, Patent Literature 1 discloses an agent for inhibiting skin yellowness, which consists of a pumpkin seed extract, while Patent Literatures 2 and 3 disclose external dermal agents which contain a plant extract having an inhibitory effect on skin yellowness. Thus, conventionally known agents, including those which are disclosed in Patent Literatures 1 to 3, are the ones for avoiding skin yellowness by inhibiting denaturation, i.e., saccharification or Maillard reaction, of proteins in the skin.

Patent Literature 4 discloses a carbonyl-inhibitor for proteins, which contains one or more effective ingredients selected from an olive leaf extract, hydrolyzed pear protein, and lemon extract, and which inhibits neither glycation reaction nor Maillard reaction but inhibits carbonylation so as not to induce yellowness in the skin.

As described above, conventional measures against skin yellowness are agents for inhibiting saccharification or Maillard reaction of proteins in the skin so as not to induce yellowness in the skin, meaning that they are so to speak agents for preventing skin yellowness. Thus, it has been made efforts for inhibiting the formation of skin yellowness because it has been recognized in the art that the once-generated skin yellowness could not be diminished to restore the skin to its original condition.

RELATED ART LITERATURES

Patent Literatures

Patent Literature 1: Japanese Patent Kokai No. 2007-254345
Patent Literature 2: Japanese Patent Kokai No. 2006-273811
Patent Literature 3: Japanese Patent Kokai No.
Patent Literature 4: Japanese Patent Kokai No. 2012-31106
Patent Literature 5: Japanese Patent Kokai No. 70994/98

SUMMARY OF THE INVENTION

Technical Problem

The present invention has an object to provide an external dermal agent for not suppressing the formation of skin yellowness but reducing skin yellowness already generated in the skin, and the above object per se is novel.

Solution to Problem

To overcome the above object, the present inventors continued intensive researches and made efforts. As a result, they newly found that the external dermal application of hesperetin and/or glycosyl hesperetin to the skin effectively reduces the already-generated skin yellowness that has been thought difficult to be reduced, and they established the uses of the above ingredients and accomplished the present invention. The term "external dermal application" as referred to as in the specification means that the external dermal agent for reducing skin yellowness according to the present invention is allowed to contact with a desired part of the skin of a subject to permeate the effective ingredient(s) of the agent into the epidermis, dermis, and/or subcutaneous tissues, wherein the skin means membranes that cover the human body surfaces having skin adnexa such as sweat glands, sebaceous glands, nails, and body hairs. Examples of means for contacting the external dermal agent for reducing skin yellowness of the present invention include applying, spraying, placing, attaching, glueing, adhering, pressing, soaking, etc.

To solve the above object, the present invention provides an external dermal agent for reducing the already-generated skin yellowness, which contains hesperetin and/or glycosyl hesperetin as an effective ingredient(s) and which is called simply "the external dermal agent for reducing skin yellowness of the present invention" hereinafter, unless specified otherwise.

The term "hesperetin" as referred to as in the specification means a compound that is represented by Chemical Formula 1 below, contained in fruits of the genus *Citrus*, and known to exert a physiological function such as a blood-flow-improving effect even when used in a relatively lesser amount.

[Chem. 1]

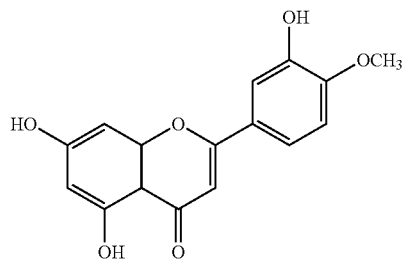

Hesperetin (Chemical Formula 1)

The term "glycosyl hesperetin(s)" as referred to as in the specification means a compound(s) in general, wherein a saccharide(s) is/are bound to hesperetin, i.e., those in general having a hesperetin skeleton. Concrete examples of such compounds include hesperidin, 7-O-β-glucosyl hesperetin having the structure of hesperidin from which the rhamnose residue as a constituent of rutinose in the hesperidin is released, and α-glycosyl hesperidins composed of hesperidin to which at least an equimolar saccharide, such as D-glucose, D-fructose, or D-galactose, is linked together via the α-linkage.

In particular, hesperidin, also called as vitamin P, is a compound represented by the following Chemical Formula 2 having the structure, where rutinose composed of rhamnose and glucose binds to hesperetin; and it is an ingredient abundantly contained in the pericarps of citrus fruits, etc.

[Chem. 2]

Chemical Formula 2

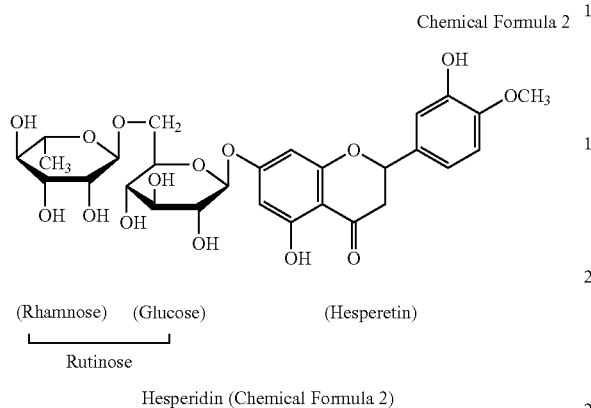

(Rhamnose) (Glucose) (Hesperetin)

Rutinose

Hesperidin (Chemical Formula 2)

7-O-β-Glucosyl hesperetin, which is a compound represented by the following Chemical Formula 3, has a characteristically higher water solubility than that of hesperidin. As shown in, for example, Patent Literature 5, 7-O-β-glucosyl hesperetin is produced by allowing α-L-rhamnosidase (EC 3. 2. 1. 40), etc., to act on a solution containing hesperidin and α-glucosyl hesperidin.

[Chem. 3]

Chemical Formula 3

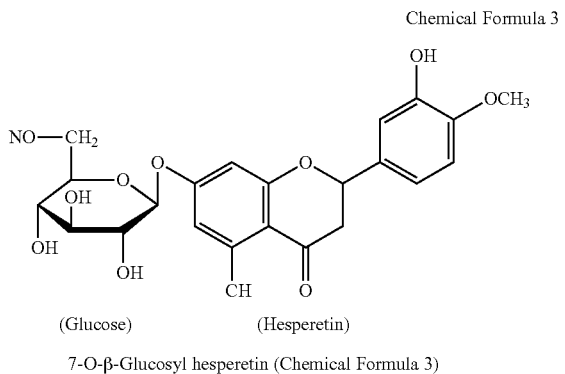

(Glucose) (Hesperetin)

7-O-β-Glucosyl hesperetin (Chemical Formula 3)

Further, α-glycosyl hesperidin is a compound composed of hesperidin to which at least an equimolar saccharide, such as D-glucose, D-fructose, or D-galactose, binds together via the α-linkage. As a representative example of α-glycosyl hesperidin, it can be mentioned α-glucosyl hesperidin represented by the following Chemical Formula 4, where a single molecule of glucose binds to the glucose residue in the rutinose structure of hesperidin, also known as an enzyme-treated hesperidin, glycosyl hesperidin, water-soluble hesperidin, or glycosyl vitamin P.

[Chem. 4]

Chemical Formula 4

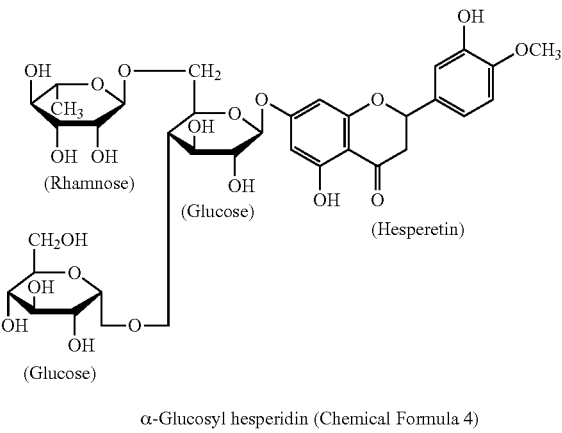

(Rhamnose) (Glucose) (Hesperetin)

(Glucose)

α-Glucosyl hesperidin (Chemical Formula 4)

The above-mentioned hesperetin and glycosyl hesperetins are compounds that have been commonly used as materials for food products, etc., and are safe and highly versatile compounds. Among such glycosyl hesperetins, α-glycosyl hesperidin has a higher water-solubility and advantageous handleability than those of hesperidin and 7-O-β-glucosyl hesperetin, and exerts the physiological activities inherent to hesperetin in living bodies, after hydrolyzed into hesperetin by the action of in vivo enzymes, similarly as in hesperidin and 7-O-β-glucosyl hesperetin.

Advantageous Effects of Invention

The external dermal agent for reducing skin yellowness of the present invention, which contains hesperetin and/or a glycosyl hesperetin(s) as an effective ingredient(s), is an agent for reducing the already-generated skin yellowness, where such reduction has been recognized to be impossible. According to the external dermal agent for reducing skin yellowness of the present invention not only reduces skin yellowness but also exerts an action of improving skin texture, as well as exerting advantageous effects of improving skin quality such as skin dryness, erythema, feeling of stimulation, and itching sensation based on the action of hesperetin and/or glycosyl hesperetin as the effective ingredients of the external dermal agent. Particularly, the external dermal agent for reducing skin yellowness of the present invention has advantageously characteristic features of more distinctly exerting the desired effects and functions, when subjects, who are anxious for their skin roughness and skin quality reduction as well as their skin yellowness, externally apply the external dermal agent to any part of their skin with any of the above-mentioned anxiety. The external dermal agent for reducing skin yellowness of the present invention has an advantageous merit of being provided safely on an industrial scale, less costly, and stably because it can be used by humans daily, successively, safely, and easily, without unfavorable feeling, and the effective ingredients of the agent are provided on an industrial scale, less costly, and stably.

BRIEF DESCRIPTION OF ACCOMPANYING DRAWINGS

FIG. 1 shows a residual ratio of carbonyl bovine-serum-albumin (BSA) in the presence of a substance having an antioxidant action.

FIG. 2 shows a residual ratio of carbonyl BSA when a composition containing glycosyl hesperetin is used alone or in combination with a composition containing glycosyl naringenin.

FIG. 3 shows a residual ratio of carbonyl BSA when a composition containing glycosyl hesperetin is used alone or in combination with L-ascorbic acid 2-glucoside.

FIG. 4 shows a result obtained by subtracting the level of carbonyl protein in "stratum-corneum protein at initiating the test" from that in "stratum-corneum protein after completing the test" or "stratum-corneum protein of control after completing the test" for each subject in the experiment of carbonyl protein reduction action using test solutions (the present invention) or a control solution (control), and treating the resulting data with a statistical procedure (one-sided t-test, $p<0.05$).

FIG. 5 shows a result obtained by calculating the ratio [(Carbonyl protein level in stratum-corneum protein after completing the test)/(Carbonyl protein level in stratum-corneum protein at initiating the test)] in terms of the level of carbonyl protein in "stratum-corneum protein after completing the test" or "stratum-corneum protein of control after completing the test" for each subject in the experiment of carbonyl protein reduction action using test solutions (the present invention) or a control solution (control), and treating the resulting data with a statistical procedure (one-sided t-test, $p<0.05$).

MODE FOR CARRYING OUT THE INVENTION

The following explain the preferred embodiments of the present invention, which just merely exemplify the preferred embodiments for practicing the present invention and should never restrict the present invention.

The term "hesperetin and/or a glycosyl hesperetin(s)", contained as an effective ingredient(s) in the external dermal agent for reducing skin yellowness of the present invention means those which can be externally applied to humans daily, successively, safely, and easily without any unpleasant feeling, and exerts the desired effects and functions of the present invention; and any of which can be used independently of their origins, processes (i.e., production methods), purities, etc., without any specific restriction. Since the present invention does not relate to a process for producing hesperetin or glycosyl hesperetin per se, detailed descriptions of such a process are omitted from the specification; however, it can be outlined as follows:

Any hesperetins, prepared from fruits of the genus *Citrus* by conventional processes, as well as commercialized ones can be appropriately used as the effective ingredients used in the external dermal agent for reducing skin yellowness of the present invention. As described above, the glycosyl hesperetins as the effective ingredients of the external dermal agent means compounds in general that are composed of hesperetin combined with a saccharide(s). Concretely speaking, the above glycosyl hesperetins mean hesperidin, 7-O-β-glucosyl hesperetin, and α-glycosyl hesperidin, and any of those which can be obtained by conventional processes as well as commercialized ones can be used in practicing the present invention as long as they can be externally applied to humans safely and easily, without inducing any stimulation or unpleasant feeling to the skin, and provided on an industrial scale, less costly, and stably, while exerting the desired effects and functions of the present invention.

Examples of the glycosyl hesperetins, as another effective ingredients in the external dermal agent for reducing skin yellowness of the present invention, include compounds such as hesperidin, α-glycosyl hesperidin, and 7-O-β-glucosyl hesperetin. The above-identified hesperidin can be obtained in a desired amount on an industrial scale in such a manner of providing a material such as fruits, pericarps, seeds, unripe fruits, etc., of citruses as hesperidin-containing plants; and extracting hesperidin from the material with a solvent such as water and alcohols. Also, the above-identified α-glycosyl hesperidin can be obtained in a desired amount on an industrial scale and at a lesser cost as disclosed in Japanese Patent Kokai No. 346,792/99, etc., in such a manner of allowing a glycosyltransferase to act on a solution containing hesperidin and an α-glucosyl saccharide compound to form α-glycosyl hesperidin, and collecting the formed α-glycosyl hesperidin. Further, the above-identified 7-O-β-glucosyl hesperetin can be produced on an industrial scale, in a desired amount, and at a lesser cost in such a manner of allowing α-L-rhamnosidase to act on an enzymatic reaction solution containing hesperidin and α-glycosyl hesperidin, obtained by the action of a glycosyltransferase, to form 7-O-β-glucosyl hesperetin; and collecting the formed 7-O-β-glucosyl hesperetin, as disclosed in, for example, Patent Literature 5.

As described above, any hesperetin and glycosyl hesperetin, which can be obtained by conventional processes, as well as commercialized ones can be used in practicing the present invention; however, more desirable are those which have a lesser impurity or a higher purity. The following explain the reason with reference to glycosyl hesperetin.

The present inventors newly found that, apart from a reagent grade glycosyl hesperetin obtained through a crystallization step, conventional glycosyl hesperetins which contain, in addition to glycosyl hesperetins, concomitants deriving from production materials, remaining intact materials, and physiologically-acceptable ionic compounds formed as by-products during their production steps, regardless of their amounts; and which contain ingredients as causative for miscellaneous tastes, coloration, odor, etc. Throughout the specification, glycosyl-hesperetin-containing compositions, which contain glycosyl hesperetins as main ingredients and concomitants deriving from their production materials, remaining intact materials, or physiologically-acceptable ionic compounds as by-products formed during their production steps, are simply called glycosyl hesperetins hereinafter, unless specified otherwise. The glycosyl hesperetins usable in practicing the present invention, naturally enough, include high-purity glycosyl hesperetins obtained through a crystallization step.

For the purpose of overcoming the defects of conventional glycosyl hesperetins such as their miscellaneous tastes and coloration, the present inventors established the desired glycosyl hesperetins reduced in miscellaneous tastes and coloration (called "improved glycosyl hesperetins" hereinafter, unless specified otherwise) and the production method thereof, and disclosed them in Japanese Patent Application No. 2014-41066 and International Patent Application No. PCT/JP2015/056230. The improved glycosyl hesperetins have advantages in that they can be externally used without unpleasant feeling and provided on an industrial scale, less costly, and stably. Thus, they are the most suitable glycosyl hesperetins in practicing the present invention.

The following explain the process for producing the improved glycosyl hesperetins and properties thereof:

The improved glycosyl hesperetins are prepared by the process containing the steps of: (a) preparing an aqueous solution containing hesperidin and a partial starch hydrolyzate; (b) allowing a glycosyltransferase to act on the resulting aqueous solution to form a composition containing glycosyl hesperetins along with α-glucosyl hesperidin; and (c) collecting the formed composition; wherein one or more of the steps (a) to (c) are conducted in the presence of a reducing agent(s), or a reducing agent(s) is/are added to a starting material(s) before conducting one or more of the steps (a) to (c) and/or is/are added to the resulting product(s) of any one of the above steps. The following are sequential explanations of the production materials for the improved glycosyl hesperetins obtainable by the production methods with the above reducing agent(s) (wherein the glycosyl hesperetins, prepared by the above step of treatment with a reducing agent(s), may be called "products treated with a reducing agent(s)", hereinafter); as well as enzymatic reactions such as transglycosylation/saccharide-transferring reaction, treatments with reducing agents, and purification methods for the improved glycosyl hesperetins.

Although discussed later in detail, the products treated with reducing agents mean glycosyl hesperetins substantially free from furfural, meaning that they are glycosyl hesperetins significantly reduced in furfural content compared with conventional products. Concretely speaking, it means that the furfural content is usually less than 200 ppb, where one ppb means billionth, preferably less than 100 ppb, more preferably less than 50 ppb, furthermore preferably less than 30 ppb, furthermore less than 20 ppb, particularly preferably less than 15 ppb, and most preferably less than 10 ppb, when determined by the later described analytical method using a gas chromatograph mass spectrometry (abbreviated as "GC/MS analysis", hereinafter) shown in the item "(1) Furfural content" in the later described Experiment 4. Among the glycosyl hesperetins used in practicing the present invention, those which have a furfural content with a reduced level below the detection limit of GC/MS analysis are distinctly-high-quality glycosyl hesperetins that are significantly reduced in miscellaneous tastes and distinctly reduced in coloration, compared to conventional products. The glycosyl hesperetins used in practicing the present invention should not necessarily have the highest possible purity, meaning that they should not necessarily be the ones with a furfural content reduced to a level below the detection limit or the ones free from furfural. Accordingly, any glycosyl hesperetins can be used in practicing the present invention as long as they do not substantially contain furfural, and the following can be also used as long as the desired object of the present invention is attained: those which contain furfural either in a significantly lower level compared to conventional products or in a level below the detection limit.

(Production Materials)

Examples of hesperidins usable as production materials for products treated with reducing agents include any hesperidins used for producing conventional glycosyl hesperetins and high-purity hesperidins, as well as extracts and juices, deriving from hesperidin-containing plants, with a relatively low purity of hesperidin, and partially-purified products thereof, one or more of which can be appropriately used in combination.

Concrete examples of the aforesaid hesperidin-containing plants include, for example, citruses belonging to the genus *Citrus* of the family Rutaceae such as mandarins, oranges, flavorful acid citruses, mixed breed citruses, tangors, tangelos, shaddocks, and kumquats; where representative hesperidin-containing parts of the above citruses are their fruits, pericarps, seeds, unripe fruits, etc.

Examples of the partial starch hydrolyzates as the aforesaid production materials include those which form α-glycosyl hesperidin as glycosyl hesperetin through the glycosyltransferation of hesperidin, when subjected to the action of the later described glycosyltransferase: partial starch hydrolyzates such as amyloses, dextrins, cyclodextrins, maltooligosaccharides; and liquefied and gelatinized starches; one or more of which can be arbitrarily selected.

The amount of a partial starch hydrolyzate used in the later described enzymatic reaction is usually about 0.1 to about 150 folds, preferably about 1 to about 100 folds, and more preferably about 2 to about 50 folds to the amount of a material hesperidin by mass. In the enzymatic reaction, saccharides deriving from partial starch hydrolyzates are glycosyltransferred into hesperidin to efficiently form α-glycosyl hesperidin, wherein the partial starch hydrolyzates should preferably be used in an excessive amount to the hesperidin so as not to remain intact hesperidin as low as possible in an enzymatic reaction system. The reason is that, in the later described purification step, partial starch hydrolyzates and saccharides or the like deriving therefrom can be relatively easily separable from α-glycosyl hesperidin; however, since hesperidin shows the same dynamics as α-glycosyl hesperidin and it is hardly separable from α-glycosyl hesperidin, the water solubility of the resultant glycosyl hesperetin will inconveniently decrease as a whole, when intact hesperidin with a distinctly-low water solubility still remains in a considerably large amount.

(Enzymatic Reaction)

The term "enzymatic reaction" as referred to as in the present specification means an enzymatic reaction, where glycosyltransferase is allowed to act on both hesperidin and a partial starch hydrolyzate as the aforesaid production materials, for forming α-glycosyl hesperidin.

Examples of the glycosyltransferase used in the above enzymatic reaction include α-glucosidase (EC 3.2.1.20), cyclomaltodextrin glucanotransferase (EC 2.4.1.19, called "CGTase", hereinafter), and α-amylase (EC 3.2.1.1), etc. Examples of the above α-glucosidase include those which are derived from animal and plant tissues such as pig liver and buckwheat seed; and those which are derived from cultures of fungi belonging to the genera Mucor, *Penicillium*, and *Aspergillus* including *Aspergillus niger*, etc., or other cultures obtained by culturing microorganisms such as yeasts of the genus *Saccharomyces* in nutrient culture media. Examples of the CGTase include those which are derived from the genera *Bacillus, Geobacillus, Klebsiella, Paenibacillus, Thermococcus, Thermoanaerobacter, Brevibacterium, Pyrococcus, Brevibacillus*, and *Saccharomyces*. Examples of the above α-amylase include those which are derived from cultures of bacteria of the genus *Geobacillus* or fungi of the genus *Aspergillus* including *Aspergillus niger*, one or more of which can be used in an appropriate combination. Any one of natural or recombinant glycosyltransferases can be used as long as they attain the objects of the present invention, and if commercialized ones are available, they can be also appropriately used. All the above glycosyltransferases should not necessarily be used after purification, and usually they can be used even in a crude enzyme form as long as attaining the objects of the present invention.

In the case of using the above natural or recombinant glycosyltransferases, the production yield of α-glycosyl hesperidin can be increased by selecting partial starch hydrolyzates suitable for the above enzymes.

When the above α-glucosidase is used, maltooligosaccharides such as maltose, maltotriose, and maltotetraose or partial starch hydrolyzates with a dextrose equivalent (DE) of about 10 to about 70 can be suitably used; in the case of using the above CGTase, α-, β-, or γ-cyclodextrin or partial starch hydrolyzates with a DE ranging from one or lower, i.e., gelatinized starch, to about 60, i.e., partial starch hydrolyzates, can be suitably used; and in the case of using the above α-amylase, partial starch hydrolyzates with a DE ranging from one or lower, i.e., gelatinized starches, to about 30, i.e., dextrins, can be preferably used.

Examples of the hesperidin-containing solution preferably used in the enzymatic reaction include those which contain hesperidin at concentrations as high as possible; preferable are suspensions of hesperidin or solutions containing hesperidin at relatively high concentrations, prepared by dissolving hesperidin in solvents such as water either at relatively high temperatures not lower than ambient temperature or under conditions of alkaline pHs of over 7.0 using alkaline agents. As such alkaline agents, the following are suitably used; one or more of about 0.1 to about 1.0 N strongly alkaline aqueous solutions of sodium hydroxide, potassium hydroxide, sodium carbonate, calcium hydroxide, aqueous ammonia, or the like.

The concentration of hesperidin in a solution form, prepared with hesperidin and an alkaline agent(s), is usually about 0.005 w/v % or higher, preferably about 0.05 to 10 w/v %, more preferably about 0.5 to about 10 w/v %, and furthermore preferably about 1 to about 10 w/v %.

When hesperidin is used in a suspension form without using any alkaline agent, hesperidin is suspended in a solvent such as water into a suspension form, wherein the concentration of hesperidin is usually about 0.1 to about 2 w/v %, preferably about 0.2 to about 2 w/v %, and more preferably about 0.3 to about 2 w/v %.

Although the temperature and time, at which glycosyltransferase is allowed to act on hesperidin and a partial starch hydrolyzate, vary depending on the concentrations of hesperidin and a partial starch hydrolyzate used in such an enzymatic reaction, as well as on the type, optimum temperature, optimum pH, or the amount of the enzyme used, the temperature is usually about 50 to about 100° C., preferably about 60 to about 90° C., more preferably about 70 to about 90° C.; and the time is about 5 to about 100 hours, preferably about 10 to about 80 hours, and more preferably about 20 to about 70 hours.

Although the pH and temperature, at which glycosyltransferase is allowed to act on an alkaline solution with a relatively high concentration of hesperidin, vary depending on the type, optimum pH, optimum temperature, or the amount of the enzyme used, as well as on the concentration of hesperidin, they should be adjusted to a highest possible pH and temperature at which the enzyme is active; wherein the pH is about 7.5 to about 10, and preferably about 8 to about 10; and the temperature is about 40 to about 80° C., and preferably about 50 to about 80° C. Since hesperidin in an alkaline solution is susceptible to decompose, it should preferably be kept under light-shielded and anaerobic conditions as much as possible to avoid such decomposition.

When glycosyltransferase is allowed to act on hesperidin in a suspension form, the pH of the enzymatic reaction varies depending on the type, optimum temperature, optimum pH, or the amount of the enzyme used, and on the concentration of hesperidin in the suspension form; however, it is usually set to a pH ranging from about 4 to about 7, preferably about 4.5 to about 6.5.

Further, if necessary, the solubility of hesperidin before the enzymatic reaction can be increased and the glycosyltransferring or saccharide-transferring reaction on hesperidin can be facilitated by coexisting an adequate amount of one or more highly water-compatible organic solvents such as lower alcohols or lower ketones including methanol, ethanol, n-propanol, isopropanol, n-butanol, acetol, and acetone in high-hesperidin-content solutions, particularly, high-hesperidin-content aqueous solutions.

Since the amount of an enzyme and the enzymatic reaction time are closely related each other, the amount of glycosyltransferase is, in terms of economic aspects, usually appropriately set to a condition sufficient for terminating the enzymatic reaction within about 5 to about 150 hours, preferably about 10 to about 100 hours, more preferably about 20 to about 80 hours, depending on the type of the enzyme used. By using an immobilized glycosyltransferase, a desired enzymatic reaction can be appropriately proceeded by a repetition use of such enzyme in a batch-wise or consecutive manner.

If needed, the enzymatic reaction solution containing hesperidin and α-glycosyl hesperidin, obtained after the above-mentioned glycosyltransferring reaction, can be used intact or after successively purified with porous synthetic adsorbing resins and partially hydrolyzed with amylase such as glucoamylase (EC 3.2.1.3) or β-amylase (EC 3.2.1.2) to lower the number of α-D-glucosyl residues of α-glycosyl hesperidin. For example, in the case of allowing the above glucoamylase to act on the enzymatic reaction solution, α-maltosyl hesperidin or higher molecules can be hydrolyzed to form and accumulate α-glucosyl hesperidin along with glucose. While, in the case of allowing the above β-amylase to act on the enzymatic reaction solution, α-maltotriosyl hesperidin or higher molecules can be hydrolyzed to form and accumulate a mixture of α-glucosyl hesperidin and α-maltosyl hesperidin along with maltose.

Glycosyl hesperetin with a relatively-high water solubility as a whole can be prepared by allowing glucoamylase and α-L-rhamnosidase simultaneously at once or successively in a random order to act on an enzymatic reaction solution containing hesperidin and α-glycosyl hesperidin obtained after the glycosyltransferring reaction, whereby equimolar or more glucoses linked via α-linkage to the glucose in the rutinose structure of α-glycosyl hesperidin are released to convert α-glycosyl hesperidin into α-glucosyl hesperidin, resulting in an increment of the content of α-glucosyl hesperidin and a conversion of hesperidin with a relatively-low water solubility into 7-O-β-monoglucosyl hesperetin with a relatively-high water solubility.

Similarly as in glycosyltransferase, glucoamylase and α-L-rhamnosidase have also a close relationship between their enzyme amounts and enzymatic reaction times, and usually, in view of economic aspects, the amount of any of the above enzymes used is preferably set to a level sufficient for terminating their enzymatic reactions within about 5 to about 150 hours, preferably about 10 to about 100 hours, more preferably about 20 to about 80 hours, depending on the types of the enzymes used. By using an immobilized α-L-rhamnosidase, a desired enzymatic reaction can be appropriately conducted repeatedly in a batch-wise or conducted continuously in a consecutive manner.

(Treatment with Reducing Agent)

The term "treatment with reducing agent" as referred to as in the present specification means a treatment for significantly or distinctly reducing miscellaneous tastes and coloration (may be abbreviated as "miscellaneous-tastes/coloration", hereinafter), as well as odor of glycosyl hesperetin, with a prescribed reducing agent(s); or a prescribed amount of the later described reducing agent(s) is/are either used in one or more of the following steps of (a) preparing an aqueous solution containing hesperidin and a partial starch hydrolyzate, (b) allowing glycosyltransferase to act on the resulting aqueous solution to form a glycosyl hesperetin containing composition with α-glucosyl hesperidin, and (c) collecting the formed composition; or added to the starting material (s) prior to one or more of the above steps (a) to (c) and/or added to the resulting products in these steps.

The reducing agents usable in the method for producing the improved glycosyl hesperetins should not specifically be restricted as long as they attain the desired objects of the present invention, and there can be used any conventional organic or inorganic reducing agents generally used in the art. Since the glycosyl hesperetins, including products treated with reducing agents, or high-purity glycosyl hesperetins usable in practicing the present invention are presupposed to be used primarily for humans, reducing agents which are high in safety and superior in stability and handleability are desirably used in producing the glycosyl hesperetins.

Concrete examples of the reducing agents preferably used in the above method include inorganic reducing agents such as hydroxylamines, chlorine dioxide, hydrogen, hydrogen compounds (including hydrogen sulfide, sodium borohydride, lithium aluminum hydride, potassium aluminum hydride, etc.), sulfur compounds (including sulfur dioxide, thiourea dioxide, thiosulfate, sulfite, ferrous sulfate, sodium persulfate, potassium persulfate, ammonium persulfate, calcium sulfite, etc.), nitrite, tin chloride, ferrous chloride, potassium iodide, hydrogen peroxide, diluted benzoyl peroxide, hydroperoxide, and chlorite such as sodium chlorite; and organic reducing agents such as phenols, amines, quinones, polyamines, formic acid and salts thereof, oxalic acid and salts thereof, citric acid and salts thereof, thiourea dioxide, hydrazine compounds, reducing saccharides, benzoyl peroxide, benzoyl persulfate, diisobutylaluminum hydride, catechin, quercetin, tocopherol, gallic acid and esters thereof, ethylenediaminetetraacetate (EDTA), dithiothreitol, reduced glutathione, and polyphenols. One or more of the above organic and inorganic reducing agents can be used in appropriate combinations.

Among the above inorganic and organic reducing agents, the former more significantly reduces the miscellaneous tastes inherent to glycosyl hesperetin without treatment with any reducing agent and provides high-quality glycosyl hesperetins that are more distinctly reduced in coloration and unpleasant odor. The reason is not sure but it can be speculated as follows: It presumes that, compared to inorganic reducing agents, organic reducing agents are low in ability of reducing miscellaneous tastes and coloration or they are in themselves organic substances susceptive to cause miscellaneous-tastes/coloration, and their decompositions, modified products, and the like are still remained in the resulting products without being completely removed in the purification steps for products treated with reducing agents, and are susceptible to affect negative influences on the quality of glycosyl hesperetin as a final product.

Among the inorganic reducing agents, what they call subsulfates (may be called sulfites) that are composed of a metal ion and $SO_2^-$, $HSO_3^-$, $SO_3^{2-}$, $S_2O_4^{2-}$, or $S_2O_7^{2-}$ ion are superior in safety, stability, and handleability and more preferably used as reducing agents in practicing the present invention. In particular, the following inorganic reducing agents can be most preferably used in practicing the present invention: subsulfates such as sodium sulfite, potassium sulfite, sodium hydrogen sulfite, sodium hyposulfite, potassium hyposulfite, sodium pyrosulfite, potassium pyrosulfite, sodium metasulfite, potassium metasulfite, sodium metabisulfite, and potassium metabisulfite.

The above-mentioned reducing agents are used in any one of the steps of producing the improved glycosyl hesperetin, or used in the starting material before any of the steps and/or the resulting product after any of the steps; however, the desired objects of the present invention can be attained with a more lesser amount of the reducing agent(s), when the agent(s) is/are used in portions in two or more of the steps or added to the starting material(s) before practicing any of the steps and/or added to the resulting product(s) after any of the steps.

The total additive amount of the above reducing agent(s), used in the above respective steps (a) to (c), is usually at least 0.001% by mass ("% by mass" is hereinafter abbreviated as "%", unless specified otherwise), preferably 0.01 to 3%, more preferably 0.01 to 1%, and furthermore preferably 0.01 to 0.5% to the mass of the enzymatic reaction solution, obtained after the above step (b) or obtained after completion of all the enzymatic reactions whenever any enzyme(s) other than glycosyltransferase is/are used. In the case of adding the reducing agent(s) to any of the previous steps before the step (c), the remaining reducing agent(s) is/are usually, substantially removed in the purification step; accordingly, no reducing agent is substantially detected in the resulting improved glycosyl hesperetin obtained as a final product. The total amount of the reducing agents, added at once or in several batches during the above steps, is usually at least 0.001% by mass, preferably at least 0.01%, and more preferably 0.01 to 1% to the mass of the enzymatic reaction solution obtained after the above enzymatic reaction. Referring to the temperatures at which the reducing agent(s) is/are added, they usually mean the temperatures employed in the above steps (a) to (c), or optionally include other temperatures exceeding the above temperatures. Concrete examples of such temperatures are those which are not lower than ambient temperature, preferably temperatures of at least 50° C., more preferably at least 70° C., more preferably at least 80° C., and furthermore preferably 90 to 120° C.

(Purification Method)

The enzymatic reaction solutions thus obtained can be preferably used intact as the improved glycosyl hesperetin of the present invention; however, they are usually prepared into glycosyl hesperetins in the form of a liquid, solid, or powder by appropriately employing either alone or in combination with one or more means of separation methods, filtration methods, purification methods using porous synthetic resins, concentration methods, spraying methods, drying methods, etc., all of which are conventionally known in the art.

Examples of the above porous synthetic resins mean synthetic resins which have a porous and large surface area and which are non-ionic: styrene-divinyl benzene copolymers, phenol-formalin resins, acrylate resins, and methacrylate resins; resins with trade names of AMBERLITE XAD-1, AMBERLITE XAD-2, AMBERLITE XAD-4, AMBERLITE XAD-7, AMBERLITE XAD-8, AMBERLITE XAD-11, AMBERLITE XAD-12, etc., commercialized by Rohm & Hass Company, Philadelphia, U.S.A.; resins with trade names of DIAION HP-10, DIAION HP-20, DIAION HP-30, DIAION HP-40, DIAION HP-50, DIAION HP-2MG, SEPABEADS SP70, SEPABEADS SP207, SEPABEADS SP700, SEPABEADS SP800, etc., commercialized by Mitsubishi Chemical Industries Ltd., Tokyo, Japan; and other resins with trade manes of IMACTI Syn-42, IMACTI Syn-44, IMACTI Syn-46, etc., commercialized by IMACTI Company, Amsterdam, the Kingdom of the Netherlands.

According to the purification methods using porous synthetic resins, glycosyl hesperetins adsorb on the porous synthetic resins, while the remaining partial starch hydrolyzates, water-soluble saccharides, etc., are eluted out from columns packed with the synthetic resins without adsorbing on the resins, when enzymatic reaction solutions are fed to the columns. In this case, hesperidin, 7-O-β-glucosyl hesperetin, and α-glycosyl hesperidin as glycosyl hesperetins usually behave similarly, and therefore, they could not be separated one another whenever the porous synthetic resins are used; however, although the handlings become complicated and the yields decrease, glycosyl hesperetins, which are selectively adsorbed on columns packed with any of the porous synthetic resins, are washed with solvents such as diluted alkalis or water, followed by feeding to the columns relatively small amounts of organic solvents or mixture solutions of organic solvents and water, i.e., aqueous methanol/ethanol solutions, to firstly elute α-glycosyl hesperidin from the columns and then intact hesperidin by increasing either the feeding volumes or the concentrations of the organic solvents. The resulting eluates containing glycosyl hesperetins are evaporated to remove the remaining organic solvents, followed by concentrating the resulting solutions up to give prescribed concentrations to obtain the glycosyl hesperetins reduced in miscellaneous tastes, etc., and hesperidin content. Since the above step of eluting glycosyl hesperetins with the above-mentioned organic solvents also acts as a step of regenerating the porous synthetic resins, it enables the repetition use of such resins as a merit.

Liquid products treated with reducing agents, having an increased purity of glycosyl hesperetins, can be produced in such a manner of, after completion of the enzymatic reactions and before contacting the resulting enzymatic reaction solutions with the porous synthetic resins, for example, removing insolubles formed when the enzymatic reaction solutions are heated, removing proteinous substances or the like in the reaction solutions by treating the solutions with magnesium aluminosilicate, magnesium aluminate, etc.; or desalting the solutions with strong-acid ion-exchange resins (H-form), intermediately-basic or weakly-basic ion-exchange resins (OH-form), or the like.

Further, the above-mentioned liquid glycosyl hesperetins can be arbitrarily dried and pulverized by conventional drying methods into particulate glycosyl hesperetins preferably used in practicing the present invention.

In this way, there can be prepared products treated with reducing agents, which are significantly reduced in the peculiar miscellaneous tastes as a defect of glycosyl hesperetins that are prepared without employing any of the above treatment step with the prescribed reducing agent(s) (may be called "products without treatment with any reducing agent", hereinafter), and which are effectively reduced in coloration and odor. While, the present inventors confirmed that the miscellaneous-tastes/coloration, or odor characteristic of products without treatment with any reducing agent are not substantially changed with mere use of the above-mentioned purification methods: Conventional purification methods, which use, for example, the above-mentioned porous synthetic resins commonly used in producing products without treatment with any reducing agent, advantageously, simultaneously remove concomitants such as water-soluble salts, as well as partial starch hydrolyzates and water-soluble saccharides; however, it is hard to significantly or distinctly reduce the miscellaneous-tastes/coloration and odor that are characteristic of products without treatment with any reducing agent, regardless how to use the above purification methods. It is estimable that any causative substance of the miscellaneous tastes, etc., contained in glycosyl hesperetins, exhibits similar dynamics of adsorption on and desorption from porous synthetic resins similar to those of the glycosyl hesperetins, and thus such causative substance could not be separated from the glycosyl hesperetins.

The glycosyl hesperetin suitably used in practicing the present invention, particularly, products treated with reducing agents are being significantly reduced in miscellaneous tastes as well as in electric conductivity and the content of ionic compounds responsible for the electric conductivity. Examples of such ionic compounds include compounds such as narirutin, diosmin, and neoponcirin, which are intrinsically contained in hesperidin as a material for the glycosyl hesperetin; glucosyl narirutin, glucosyl neoponcirin, etc., as enzymatic reaction by-products, as well as decompositions thereof and compounds closely related to such decompositions; furfurals such as furfural used as an index for practicing the present invention, furfuryl alcohol, and hydroxymethyl furfural, as well as salts thereof, etc.; and other compounds that release metallic cations such as calcium, potassium, magnesium, sodium, etc., when in solution forms; all of which are derived from the production materials for the improved glycosyl hesperetin or formed as by-products during their production steps. Usually, products treated with reducing agents suitably used in practicing the present invention only slightly contain the above ingredients such as narirutin, diosmin, neoponcirin, glucosyl narirutin, and glucosyl neoponcirin. The above-mentioned ionic compounds are called physiologically acceptable ionic compounds throughout the specification.

It is uncertain that, in the above-mentioned method for producing products treated with reducing agents, the mechanism of how the improved glycosyl hesperetin, whose miscellaneous tastes and coloration, particularly, miscellaneous tastes are significantly reduced, is obtained with the prescribed reducing agents; however, it can be speculated as follows:

(1) In producing the products treated with reducing agents, the prescribed reducing agents act on substances, as potential causatives for miscellaneous tastes deriving from the production materials, to mask, decompose, or modify the substances to obtain the improved glycosyl hesperetins that are significantly reduced in miscellaneous tastes;

(2) In the step(s) of producing products treated with reducing agents, the prescribed reducing agents reduce or inhibit the formation of substances as potential causatives for miscellaneous tastes; or they mask, decompose, or modify the formed substances to obtain the improved glycosyl hesperetins that are significantly reduced in miscellaneous tastes; or (3) The substances as potential causatives for miscellaneous tastes as shown in the above items (1) and (2) are modified with the prescribed reducing agents to facilitate the separation of glycosyl hesperetin in the purification step using porous synthetic adsorbents, etc., resulting in obtaining the glycosyl hesperetins that are significantly reduced in miscellaneous tastes.

The glycosyl hesperetins suitably used in practicing the present invention further include those which are significantly reduced in miscellaneous tastes and unpleasant odor of compositions containing glycosyl hesperetins by allowing such compositions to contact with the prescribed reducing agents. Such compositions are also included in the products treated with reducing agents as referred to as in the specification. When contacted with the prescribed reducing agents, the miscellaneous tastes of such compositions are significantly reduced and the coloration and odor are effectively and distinctly lowered. Contacting compositions containing glycosyl hesperetins with the prescribed reducing agents should preferably be conducted in a solution or suspension state by using an appropriate solvent such as water, rather than in a solid state. Examples of such compositions containing glycosyl hesperetins to be contacted with the prescribed reducing agents include glycosyl hesperetins containing one or more of hesperidin, α-glycosyl hesperidin, and 7-O-β-glucosyl hesperetin. Examples of such compositions include those which contain glycosyl hesperetins in an amount of, usually, at least 50% but less than 100%, preferably at least 60% but less than 100%, more preferably at least 70% but less than 100%, particularly preferably at least 80% but less than 100%, and furthermore preferably at least 90% but less than 100%.

The same reducing agents as used in producing products treated with reducing agents can be used when allowed to be contacted with the above compositions containing glycosyl hesperetins. The amount of respective reducing agents to be added to glycosyl hesperetins is usually at least 0.00001%, preferably 0.0001 to 0.5%, more preferably 0.001 to 0.4%, and furthermore preferably 0.001 to 0.3% to the mass of the glycosyl hesperetins, on a dry solid basis (d.s.b.), wherein the resulting mixture is mixed to homogeneity to allow the glycosyl hesperetins to be contacted with the reducing agents to significantly or distinctly reduce the miscellaneous tastes, etc., as a characteristic of the glycosyl hesperetins, which even though are products without treatment with any reducing agent.

The above products treated with reducing agents in liquid form can be arbitrarily concentrated by conventional concentration methods into those in the form of a syrup or paste, or further dried by conventional drying methods into those in the form of a solid, granule, or powder.

As described above, there can be obtained products treated with reducing agents, which are significantly or distinctly reduced in miscellaneous tastes, etc., as characteristic defects of the products without treatment with any reducing agent.

Among the improved glycosyl hesperetins usable in practicing the present invention, products treated with reducing agents, which are obtained by the above production method and substantially free of furfural and 4-vinyl anisole (abbreviated as "4-VA", hereinafter, and it is also known as 4-methoxystylene), a kind of phenol ether, are more significantly reduced in miscellaneous tastes, as well as being distinctly reduced in coloration and odor; they can be most suitably used in practicing the present invention. The above-identified 4-VA, which is an ingredient that is speculated to be generated from the production materials for the improved glycosyl hesperetins, is usually contained in the resulting glycosyl hesperetins in an amount of less than 30 ppb to the mass of each of the glycosyl hesperetins, d.s.b.; among which, those with a furfural content of less than 200 ppb are characteristic in that the 4-VA content and the furfural content are usually in a direct proportional relationship. The term "substantially does not contain 4-VA" as referred to as in the present disclosure means that, similarly as for furfural, the 4-VA content is significantly low level, compared with compositions containing other glycosyl hesperetins, such as products without treatment with any reducing agent, other than products treated with reducing agents. More concretely, when determined by the analytical method using the GC/MS analyzer shown in "(2) 4-VA Content" in the later described Experiment 4, the 4-VA content in products treated with reducing agents is usually less than 30 ppb, preferably less than 15 ppb, more preferably less than 10 ppb, further preferably less than 5 ppb, moreover preferably less than 3 ppb, and furthermore preferably less than 2 ppb to the dry mass of any of the products treated with reducing agents.

Compared to products without treatment with any reducing agent, products treated with reducing agents have an advantageously characteristic feature in that coloration (may be called "coloration degree", hereinafter) is distinctly reduced. The coloration degree of glycosyl hesperetin is determined by the method shown in "(3) Color tone and coloration degree" in the later described Experiment 4 and outlined as follows: An aqueous solution having a prescribed concentration of glycosyl hesperetin is subjected to a heat treatment in a sealed container, and the resulting solution is macroscopically observed for color tone and measured for its absorbances of $OD_{420\,nm}$ and $OD_{720\,nm}$ at respective wavelengths of 420 nm and 720 nm, followed by calculating the difference between the above absorbances, i.e., $OD_{420\,nm}$ minus $OD_{720\,nm}$, to obtain a value for use as a coloration degree. Preferred embodiments of the glycosyl hesperetins used in practicing the present invention include those which have the above absorbance difference being less than 0.24, preferably 0.20 or lower, more preferably 0.17 or lower, and furthermore preferably over 0 but 0.15 or lower. In view of the fact that products without treatment with any reducing agent have a defect of being distinctly increased in their coloration degrees by heating, the above aqueous solution is to be purposefully heated in this assay to realistically evaluate the coloration of glycosyl hesperetins induced by heating.

The aforesaid products treated with reducing agents are compositions containing glycosyl hesperetins, which contain glycosyl hesperetins and physiologically acceptable ionic-compounds and have an electric conductivity of less than 10 μS/cm, preferably less than 8 μS/cm, more preferably less than 6 μS/cm, furthermore preferably over 0 μS/cm but less than 4.5 μS/cm, when determined in such a manner of being prepared into 1 w/v % aqueous solutions, heating the aqueous solutions at 100° C. for 30 min in respective sealed containers, and cooling the heated solutions to 20° C. for determining their electric conductivities.

The products treated with reducing agents, obtained by the above production method, are compositions which are mainly composed of one or more glycosyl hesperetins selected from hesperidin, α-glycosyl hesperidin, and 7-O-β-glucosyl hesperetin; more preferable are those which contain glycosyl hesperetins in a total amount of at least 90% but less than 100%, preferably at least 93% but less than 100%, more preferably at least 95% but less than 100%, moreover preferably at least 97% but less than 100%, and furthermore at least 98% but less than 100%, to the mass of each of the compositions, d.s.b.

The term "α-glycosyl hesperidin content" as referred to as in the present specification means as follows: The content of α-glycosyl hesperidin in a composition containing α-glycosyl hesperidin is determined by sampling the composition; diluting or dissolving the sample with refined water into a 0.1 w/v % solution; filtering the solution with a 0.45 μm membrane filter; subjecting the filtrate to high-performance liquid chromatography analysis (called "HPLC analysis", hereinafter) using a reagent grade hesperidin, commercialized by Wako Pure Chemical Industries, Ltd., Tokyo, Japan, as a standard substance under the conditions below; and calculating, based on dry solid basis, the contents of glycosyl hesperetins based on the areas of peaks appeared in a chromatogram at an UV wavelength of 280 nm and the molecular weights corresponding to respective peaks for glycosyl hesperetins such as hesperidin and α-glycosyl hesperidin including α-glucosyl hesperidin. The following (1) to (4) outline the quantification on HPLC analysis of the glycosyl hesperetins:

<HPLC Analysis Conditions>
HPLC Apparatus: "LC-20AD", commercialized by SHIMADZU CORPORATION, Kyoto, Japan
Degasser: "DGU-20A3", commercialized by SHIMADZU CORPORATION, Kyoto, Japan
Column: "CAPCELL PAK C18 UG 120", commercialized by Shiseido Co., Ltd., Tokyo, Japan
Sample injection volume: 10 µL
Eluant: Water/acetonitrile/acetic acid (80/20/0.01 (by volume ratio))
Flow rate: 0.7 mL/min
Temperature: 40° C.
Detection: "SPD-20A", a UV detector, commercialized by SHIMADZU CORPORATION, Kyoto, Japan
Measurement wavelength: 280 nm
Data processor: "CHROMATOPAC C-R7A", commercialized by SHIMADZU CORPORATION, Kyoto, Japan (1) Content of hesperidin: It is determined by analyzing a sample on HPLC and calculating the content of hesperidin based on the ratio of the peak area of the hesperidin in the sample to that of a reagent grade hesperidin as a standard substance, commercialized by Wako Pure Chemical Industries, Tokyo, Japan, at a prescribed concentration.

(2) Content of α-glucosyl hesperidin: It is determined by analyzing a sample on HPLC and calculating the content of α-glucosyl hesperidin based on the ratio of the peak area of the α-glycosyl hesperidin in the sample to that of a reagent grade hesperidin as a standard substance, commercialized by Wako Pure Chemical Industries, Tokyo, Japan, at a prescribed concentration; and on the molecular weight ratio of the α-glycosyl hesperidin to the hesperidin.

(3) Content of 7-O-β-glucosyl hesperetin: It is determined by analyzing a sample on HPLC and calculating the content of 7-O-β-glucosyl hesperetin based on the ratio of the peak area of the 7-O-β-glucosyl hesperetin in the sample to that of a reagent grade hesperidin as a standard substance, commercialized by Wako Pure Chemical Industries, Tokyo, Japan, at a prescribed concentration; and on the molecular weight ratio of the 7-O-β-glucosyl hesperetin to the hesperidin.

(4) Contents of other glycosyl hesperetins: It is determined by analyzing a sample on HPLC and calculating the contents of other glycosyl hesperetins based on the ratio of the peak area of each of the other glycosyl hesperetins in the sample to that of a reagent grade hesperidin as a standard substance, commercialized by Wako Pure Chemical Industries, Tokyo, Japan, at a prescribed concentration; and on the molecular weight ratios of the other α-glucosyl hesperetins to the hesperidin.

Among the products treated with reducing agents obtained by the above production method, glycosyl hesperetins containing or consisting of α-glucosyl hesperidin as α-glycosyl hesperidin are preferable because such glycosyl hesperetins more distinctly exert the desired functions and effects of the present invention, i.e., a satisfactory effect of improving the already-generated skin yellowness. Preferable contents of α-glucosyl hesperidins in the aforesaid glycosyl hesperetins are usually 60 to 90%, preferably 70 to 90%, and more preferably 75 to 90% to the solid mass of each of the above products, because the higher the lower limit of α-glucosyl hesperidin content, the more the above-identified functions and effects will be exerted distinctly.

Among the products treated with reducing agents obtained by the above production method, those which have the following properties are preferable because they more distinctly exert the desired functions and effects of the present invention, i.e., an action of reducing the already-generated skin yellowness: Any of the products treated with reducing agents have an absorbance difference, i.e., $OD_{420\ nm}$ minus $OD_{720\ nm}$, being less than 0.24, preferably 0.20 or lower, more preferably 0.17 or lower, and furthermore preferably 0 or higher but 0.15 or lower, when measured for absorbances at wavelengths of 420 nm ($OD_{420\ nm}$) and 720 nm ($OD_{720\ nm}$) with a spectrophotometer after prepared into a 1 w/v % aqueous solution and heating it at 100° C. for 30 min in a sealed container, adjusting the heated aqueous solution to give ambient temperature, and placing a sample of the aqueous solution in a 1-cm wide cuvette. Compared with glycosyl hesperetins obtained by the production methods without treatment with any of the prescribed reducing agent, the above specific products are also superior in their significantly or distinctly reduced miscellaneous-tastes/colorations, and odors.

Among the products treated with reducing agents obtained by the above production method, those which have the following properties are preferable because they more distinctly exert the desired functions and effects of the present invention, i.e., actions of improving the already-generated skin yellowness: When determined on high-frequency inductively coupled plasma emission spectrometric analysis, compositions containing glycosyl hesperetins which contain calcium, potassium, magnesium, and sodium in the amounts within the ranges below, wherein the calcium, potassium, magnesium, and sodium are contained in respective amounts of 1 ppm or lower, 0.1 ppm or lower, 0.2 ppm or lower, and 0.4 ppm or lower; more preferably in respective amounts of 0.6 ppm or lower, 0.06 ppm or lower, 0.1 ppm or lower, and 0.3 ppm or lower; and more preferably, in respective amounts of 0 ppm or more but 0.5 ppm or lower, 0 ppm or more but 0.05 ppm or lower, 0 ppm or more but 0.08 ppm or lower, and 0 ppm or more but 0.2 ppm or lower to the solid mass of each of the products treated with reducing agents. Compared to compositions containing glycosyl hesperetins obtained by conventional production methods, the above specific products are also superior in their significantly or distinctly reduced miscellaneous-tastes/colorations, and odors.

Since the products treated with reducing agents are significantly reduced in miscellaneous tastes and also distinctly reduced in coloration and odor, as well as being improved in thermostability, they are, compared with their properties just after their processings, still kept intact in miscellaneous-tastes/coloration and odor inherent to the products treated with reducing agents without causing any substantial difference or they are effectively suppressed in any increment thereof, even when heated at a high temperature of 80 to 100° C. for 30 min or longer, during the steps of being incorporated with reducing agents, or after incorporated into the external dermal agent for reducing skin yellowness and stored at ambient temperature or slightly higher temperature thereof for several tens of minutes to several months. The products treated with reducing agents also have the merits of having a satisfactory acid-tolerance and thermostability.

As described above, the glycosyl hesperetins used in practicing the present invention mean compositions which contain, as a main ingredient(s), either or both of (1) α-glycosyl hesperidin (α-glucosyl hesperidin, etc.) and (2)

hesperidin and 7-O-β-glucosyl hesperetin, i.e., mixtures of glycosyl hesperetins; and which further contain (3) flavonoids such as narirutin, diosmin, neoponcirin, and glucosyl narirutin, and (4) trace ingredients such as salts, all of which are presumed to be derived from their production materials or formed as by-products during their production processes. Among these glycosyl hesperetins, preferably used in practicing the present invention are the improved glycosyl hesperetins which contain the above ingredients (1) and (2) in a total percentage (%) (simply called "glycosyl hesperetin content") of, on a dry solid basis, at least 90% but less than 100%, preferably at least 93% but less than 100%, more preferably at least 95% but less than 100%, further preferably at least 97% but less than 100%, and furthermore preferably at least 98% but less than 100%. The improved glycosyl hesperetins may contain hesperetin.

The purity of the improved glycosyl hesperetins used in practicing the present invention or the upper limit of the glycosyl hesperetin content in the glycosyl hesperetins, d.s.b., is usually 99% that facilitates an industrial production of the glycosyl hesperetins in a relatively large amount and at a lesser cost; preferably those with 98% can be provided at a more lesser cost, and more preferably those with a content as low as 97% or lower can be provided at a furthermore lesser cost. The lower the glycosyl hesperetin content in the glycosyl hesperetins, d.s.b., the more the glycosyl hesperetins should be inevitably used compared with those with a higher glycosyl hesperetin content, resulting in complicated handling and poor handleability. Accordingly, the lower limit of the glycosyl hesperetin content should usually be at least 90%, preferably at least 93%, more preferably at least 95%, moreover preferably at least 97%, and furthermore preferably at least 98%.

More preferred embodiments of the improved glycosyl hesperetins used in practicing the present invention include, for example, those with an α-glycosyl hesperidin content of at least 50% but less than 100%, d.s.b., among those which contain, as glycosyl hesperetin, α-glycosyl hesperidin such as α-glucosyl hesperidin.

In the case of providing the external dermal agent for reducing skin yellowness of the present invention at a more lesser cost, the upper limit of the α-glucosyl hesperidin content in the improved glycosyl hesperetins used in practicing the present invention should preferably be, usually, 90% or lower, and those with such content can be easily provided on an industrial scale in a relatively larger amount and at a lesser cost; preferably those with a content of 85% or lower can be provided at a more lesser cost, and more preferably those with a content of 80% or lower can be provided at a furthermore lesser cost. Due to a similar reason as mentioned in the above glycosyl hesperetin content, the lower limit of α-glucosyl hesperidin content in the improved glycosyl hesperetins should usually be 60% or higher, preferably 65% or higher, and more preferably 70% or higher.

The external dermal agent for reducing skin yellowness of the present invention can be incorporated with other ingredients than the hesperetin and/or glycosyl hesperetins as the effective ingredient(s). Examples of the other ingredients include naringenin, glycosyl narigenins such as naringin and glucosyl naringin; L-ascorbic acids such as L-ascorbic acid and its salts and derivatives including L-ascorbic acid 2-glucoside and the like; polyphenols such as resveratrol, quercetin, chlorogenic acid, anthocyanin, curcumin, kaempferol, and flavonoids; plant extracts such as *Cynara scolymus* leaf extract, *Angelica keiskei* extract, *Fragaria* seed extract, *Ginkgo biloba* leaf extract, *Citrus unshiu* extract, *Ribes nigrum* extract, *Actinidia deliciosa* extract, *Vaccinium macrocarpon* extract, *Malpighia emarginata* extract, *Emblica officinalis* extract, and *Aronia* extract; carotenoids such as astaxanthin and β-carotene; plant extracts or compounds having an action of inhibiting glycation per se (called "glycation-reaction-inhibitory action"); and saccharides; organic acids; and amino acids. Particularly, the hesperetin and/or the glycosyl hesperetins as the effective ingredient(s) of the external dermal agent for reducing skin yellowness of the present invention cooperatively and effectively exert an action of reducing skin yellowness when used with one or more of the following ingredients: naringenin, glycosyl naringenin including naringin and glucosyl naringin; L-ascorbic acids; saccharides such as mannitol, N-acetyl glucosamine, maltose, maltotriitol, raffinose, and maltotetraose; organic acids such as lactic acid, malic acid, tartaric acid, citric acid, salicylic acid, ferulic acid, glucuronic acid, gluconic acid, glucuronolactone, sorbic acid, and benzoic acid; and amino acids such as glycine and sodium glutamate. The above-identified other ingredients either effectively enhance the action of reducing skin yellowness exerted by the hesperetin and/or glycosyl hesperetins as the effective ingredients of the external dermal agent for reducing skin yellowness of the present invention, or additively or synergistically exert the action of reducing the desired skin yellowness along with the action of reducing skin yellowness exerted by the ingredients per se.

Examples of plant extracts or compounds having a glycation-inhibitory action include extracts of plants such as *Euphrasia officinalis*, *Pilea mongolica*, *Elaeagnus umbellata*, *Agrimonia eupatoria*, *Agni* fruit, *Akebia quinata*, fruit of *Euterpe oleracea*, *Withania somnifera*, *Thujopsis dolabrata*, *Acacia catechu*, *Quercus variabilis*, *Gynostemma pentaphyllum*, *Pimpinella anisum* L., *Hamamelis virginiana*, *Alistin*, *Epimedium grandiflorum* var. *thunbergianum*, *Fallopia japonica* (Houtt.) Ronse Decr. var. *japonica*, *Ginkgo biloba*, *Pyrola japonica*, *Fragaria*, *Lilium tenuifolium* Fischer, *Gloiosiphonia capillaris*, *Ficus erecta*, bark of *Tabebuia* spp., *Acer palmatum*, *Lilium maculatum* Thunb., *Foeniculum vulgare*, *Hamamelis virginiana*, *Gaultheria procumbens*, *Curcuma longa* Linn, *Prunus mume*, *Quercus salicina*, *Epimedium brevicornum* Maxim, dried fruit of *Rosa multiflora*, *Echinacea angustifolia*, *Eleutherococcus senticosus*, *Cytisus scoparius*, *Gentianella alborosea* (Gilg) Fabris, *Sambucus nigra*, *Ilex paraguariensis*, *Borassus flabellifer*, *Phellodendron amurense*, *Coptis japonica* (Thunb.) Makino, *Silybum marianum*, *Avena sativa*, *Cardamine scutata*, *Salsola komarovii*, *Lilium rubellum*, *Lapsana apogonoides*, *Lilium lancifolium*, *Origanum vulgare*, *Citrus sinensis*, seed of *Cucurbita*, bark of *Erythroxylum catuaba*, *Lilium speciosum*, *Paullinia cupana*, *Hibiscus sabdariffa*, *Asarum nipponicum*, *Tussilago farfara*, *Platycodon grandiflorus*, *Rumex japonicus*, *Clerodendron trichotomum*, *Mallotus philippinensis*, *Lilium medeoloides* A. Gray, *Juglans*, *Vaccinium vitis-idaea* L., *Monochoria vaginalis* var. *plantaginea*, *Eisenia arborea* J. E. Areschoug, *Punica granatum*, *Ipomoea batatas*, *Smilax regelii* Killip & Morton, *Crataegus cuneata*, *Pellionia minima*, *Perilla frutescens* var. *crispa*, *Psophocarpus tetragonolobus* (L.) D.C., *Filipendula multijuga*, *Paeonia lactiflora*, *Rheum palmatum*, *Aster scaber*, *Chenopodium album*, *Aster ageratoides* ssp. *Leiophyllus*, *Plantago major*, *Centella asiatica*, *Fagopyrum esculentum*, *Lilium formosanum* A. Wallace, *Cardamine scutata* Thunb., *Davilla rugosa*, *Lilium nobilissimum* Makino, *Cordia salicifolia*, *Syzygium aromaticum* Merr. et Perry, *Cassia angustifolia*, *Centella asiatica* (L.) Urb., *Bellis perennis*, *Anethum graveolens*, *Harpogophytum procumbens*, *Farfugium*

*japonicum* (L.) Kitam, *Lilium longiflorum*, root of *Harpogophytum procumbens*, *Rubus suavissimus* S. Lee, *Prunus persica*, *Houttuynia cordata*, *Rosa roxburghii*, leaves of *Eucommia ulmoides*, *Solanum lycopersicum*, *Potentilla tormentilla* Schrk (Rosaceae), *Rumex crispus*, *Sambucus racemosa* subsp. *sieboldiana*, *Trapaeolum majus* Linn., *Aster microcephalus* var. *ovatus*, *Mentha*, *Lilium longiflorum*, *Lespedeza*, *Colocasia gigantea*, *Passiflora incarnata*, *Passiflora edulis* Sims, roots of *Pfaffia*, *Artocarpus heterophyllus*, *Prunus cerasoides* var. *campanulata*, *Helianthus annuus*, *Elatostema japonicum* var. *japonicum*, *Lilium concolor*, *Lapsana* spp., *Areca catechu*, *Petasites japonicus* (Siebold et Zucc.) Maxim, *Lablab purpureus* (L.) Sweet, *Cimicifuga racemosa*, *Crassocephalum crepidioides*, *Actinidia polygama*, *Machilus odoratissima*, *Pinus*, *Lithocarpus edulis*, *Ilex paraguariensis*, *Lilium candidum*, achenes of *Silybum marianum*, *Staphylea bumalda*, *Stauntonia hexaphylla*, *Nemacystus decipiens*, *Salicaceae*, *Hemerocallis fulva* var. *kwanso*, *Annona montana* Macfady, *Lilium auratum*, *Ipomoea aquatica*, *Aster yomena*, seeds of *Litchi chinensis*, *Lilium regale*, *Pleioblastus linearis*, *Rubus rosaefolius*, unripe fruit of *Malus pumila*, flowers of *Tilia cordata*, *Aspalathus linearis*, *Lactuca sativa*, *Citrus limon*, *Cymbopogoncitratus*, *Thymus X citriodorus*, *Aloysia citrodora*, *Melissa officinalis*, *Rosa canina*, flower buds of *Rosa damascena*, *Rosmarinus officinalis* L., *Rosa X centifolia* L., *Laurus nobilis*, *Aerides rosea*, *Haematoxylum campechianum*, *Sanguisorba officinalis*, *Astragalus sinicus*, leaves of *Diospyros kaki* Thunberg, leaves of *Glycyrrhiza uralensis*, episperms of *Glycine max*, seeds of *Oryza sativa* subsp. *javanica*, leaves of *Alpinia zerumebet*, *Liliumtenuifolium* Fischer, *Salix* sp., and leaves of *Eucommia ulmoides*; extracts of sea algae such as *Gloiopeltis complanata* (Harvey) Yamada, *Gloiopeltis furcata* (Postels et Ruprecht) J. Agardh, and *Gloiopeltis tenax* (Turner) J. Agardh; extracts of raw coffee beans, lees of liquor distilled from sweet potatoes, mycelia of *Agaricus blazei*, etc.; equol; isoflavone; 1,4-anthraquinone; 1-amino-2-hydroymethyl anthraquinone; 4-aminophenol; 1,3,5-trihydroxybenzene, kojic acid; 3,4-dihydroxy-phenylacetate; caffeine acid; ifenprodil; 6-hydroxy-2,5,7,8-tetramethylchroman-2-carboxylate; 6-hydroxyindole; 7-hydroxy-4,6-dimethylphthalide; α-lipoic acid, 4-hydroxychalcone; protein hydrolyzates of pearls; aminoguanidine, erythrosine sodium, L-ergothioneine, resveratrol; hydroxystilbenes such as 3,3',5,5'-tetrahydroxystilbene; oxindole; carnosine; salicylic acid; salsolinol hydrobromide; sinapinic acid; tocopherylnicotinate; nicotinic-acid amide; nordihydroguaiaretic acid; proanthocyanin; mannitol; hydrolyzed casein; hydrolysable tannin; catechol; chlorogenic acid and derivatives thereof such as chlorogenic acid, isochlorogenic acid, neochlorogenic acid, cryptochlorogenic acid, and feruloyl caffeoylquinic acid; and others such as leucocyanidin, prunin, procyanidol oligomer, and glycosylrutin. Among the above ingredients, the following are exemplified as plant extracts or compounds, having a glycation-inhibitory action, suitably used in practicing the present invention: Extracts of *Withania somniferous*, *Thujopsis dolabrata*, *Acacia catechu*, *Ginkgo biloba*, *Gaultheria procumbens*, *Phellodendron amurense*, *Citrus sinensis*, seeds of *Cucurbita*, barks of *Erythroxylumcatuaba*, *Mallotus philippinensis*, glucosyl rutin, *Vacciniumvitis-idaea* L., *Perilla frutescens* var. *crispa*, leaves of *Fagopyrum esculentum*, *Davilla rugosa*, *Houttuynia cordata*, *Elatostema japonicum* Wedd., *Crassocephalum crepidioides*, *Actinidia polygama*, *Pleioblastus linearis*, *Rubus croceacanthus*, unripe fruit of *Malus pumila*, leaves of *Diospyros kaki* Thunberg, leaves of *Glycyrrhiza glabra* (licorice), leaves of *Alpinia zerumbet*, and extracts of leaves of *Eucommia ulmoides*, as well as equol, isoflavone, ifenprodil, protein hydrolyzates of pearls, catechol, caffeic acid, and prunin. Respective contents of the above-mentioned other ingredients to be incorporated into the external dermal agent for reducing skin yellowness of the present invention are usually 0.001% or more, preferably 0.01 to 50%, more preferably 0.01 to 30%, furthermore preferably 0.01 to 20%, and furthermore preferably 0.01 to 10% to the total mass of the agent.

The external dermal agent for reducing skin yellowness of the present invention can be optionally in the form of, for example, a powder, solid, liquid, cream, or paste. Examples of such forms include ointments, milky lotions, creams, tablets, granules, powders, sprays, suspensions, pastes, jellies, liquids, gels, bath salts, lotions, body oils, essences, face powders, packs, etc. Examples of the methods for incorporating hesperetin and/or glycosyl hesperetins into the external dermal agent for reducing skin yellowness include, for example, admixing, kneading, mixing, adding, dissolving, soaking, permeating, sparging, applying, spraying, injecting, etc., one or more of which can be used in any steps before completing the preparation of the external dermal agent.

The external dermal agent for reducing skin yellowness of the present invention can be exemplified in the form of a cosmetic, pharmaceutical, or quasi-drug as mentioned in the above, and it can be arbitrarily used after incorporated into cosmetics in an adequate amount.

The amount of hesperetin and/or glycosyl hesperetins contained in the external dermal agent for reducing skin yellowness of the present invention can be appropriately set to a desired level, depending on the application frequency of the agent and the skin conditions of users; however, when one or more of hesperetin and/or glycosyl hesperetins are all regarded as hesperetin upon calculation of their amounts (simply called "hesperetin conversion", hereinafter), they can be incorporated into the agent in a total amount of over 0.0001% but less than 100%, preferably over 0.001% but less than 100%, more preferably 0.01% or more but less than 100%, furthermore 0.01 to 60%, furthermore preferably 0.01 to 40%, and furthermore preferably 0.01 to 20%, d.s.b. A preferable external application frequency and term of the external dermal agent for reducing skin yellowness of the present invention are usually, successively one to five times a day, preferably one to three times a day (in the morning, at noon, or in the evening/night) for at least several days, preferably at least several weeks, more preferably at least one month, furthermore at least two months, furthermore preferably at least three months daily or at an interval of at least one day. When the dose is below the above lower limit, the desired functions and effects of the present invention distinctly lower or even become invalid; while when the dose is over the above upper limit, the right functions and effects commensurate with such overdose may not be exerted and it is also not preferable in terms of an economical viewpoint. The external dermal agent for reducing skin yellowness is preferably applied to the outer skin, particularly, to the skin excluding mucosae.

Even when kept or stored at an ambient temperature or a slightly higher temperature thereof for tens of minutes to several months, the external dermal agent for reducing skin yellowness of the present invention thus obtained per se and compositions incorporated therewith are reduced in odor to a level completely free of odor or even to an unnoticeable level.

The external dermal agent for reducing skin yellowness of the present invention is further explained in more detail with reference to the following experiments:

<Experiment 1: Selection of Substances Capable of Reducing Carbonyl Protein>

(1) Summary

It is known that the skin becomes apparently to show subdued yellowness, i.e., skin yellowness is induced, when proteins in the deeper part of the dermis of the skin are denatured/carbonylated by peroxides, etc. In this experiment, substances capable of reducing skin yellowness were selected by using the later described carbonyl protein model.

(2) Carbonyl Protein Model

A carbonyl protein, obtained by carbonylating bovine serum albumin (termed "BSA", hereinafter), was prepared as a carbonyl protein model (termed "carbonyl BSA", hereinafter) and used in this experiment.

<Preparation of Carbonyl BSA>

In phosphate buffered saline (termed "PBS (-)", hereinafter) containing 100 μM of sodium hypochlorite as a carbonyl initiator was dissolved BSA to give a final concentration of 40 mg/mL, followed by keeping the resulting solution at 37° C. overnight to form carbonyl BSA, as a carbonyl protein model, used as a substance to cause skin yellowness, and removing the remaining sodium hypochlorite with "AMICON ULTRA 10K", a product name of ultrafiltration membrane, commercialized by Merck Millipore Corporation, Tokyo, Japan, to obtain a carbonyl BSA. In this experiment, the carbonyl BSA was used as a carbonyl protein model.

(3) Test Sample

The following were used as test samples: a particulate composition containing glycosyl hesperetin obtained in the later described Example 1 (simply called "composition containing glycosyl hesperetin", hereinafter); a composition containing glycosyl naringenin or a composition containing 67.6% of monoglucosyl naringin and 22.4% of naringin prepared by the method disclosed in Japanese Patent No. 3967563; "AA2G", a product name of L-ascorbic acid 2-glucoside commercialized by Hayashibara Co., Ltd., Okayama, Japan; a special-reagent-grade niacinamide with a purity of 98.0% or higher, commercialized by Wako Pure Chemical Industries, Ltd., Osaka, Japan; and a reduced glutathione with a purity of 99% or higher, commercialized by Sigma Aldrich Co., LLC, Osaka, Japan.

(4) Selection of Substances Having an Action of Reducing Carbonyl Protein or an Action of Reducing Skin Yellowness (a Sole Use Test)

By using a well-known anti-carbonyl test being used as a method for selecting substances capable of inhibiting the formation of carbonyl proteins, the present inventors examined the test samples as listed in Table 1 for their carbonyl protein reduction actions according to the following procedures: A 100 μL solution containing 10 mg/mL of the carbonyl BSA, prepared in the above (2), was added to PBS (-) to give a total volume of one milliliter in which any one of the test samples in the above (3), as candidates for substances capable of inhibiting the formation of carbonyl protein, was dissolved to give a concentration of 0.1 w/v %. The whole content of a solution, containing the carbonyl BSA prepared in the above (2) and anyone of the test samples in a mass ratio of 1:1 (called "a test solution for carbonyl protein reduction test", hereinafter), was kept at 37° C. for 16 hours and filtered with the above ultrafiltration membrane, followed by removing the remaining antioxidants. Based on Western blot analysis, the concentration of carbonyl BSA was assayed with dot blot method using a kit, "OxyBlot™ Protein Oxidation Detection Kit", a product name of a kit for analyzing the oxidation level of protein, commercialized by Merck Millipore Corporation, Tokyo, Japan. The resulting measured values (emission intensity) were analyzed with "Image J", an image processing software explored by National Institutes of Health (NIH), Maryland, USA. While, a PBS (-) solution (called "control", hereinafter) containing carbonyl BSA, obtained similarly as in the above except for not using any of the test samples, was similarly measured as in the above, followed by determining the ratios of the measured values for those with the test samples against that of control. The results are in Table 1 and FIG. 1. Compared to the ratio of carbonyl BSA in control with no addition of any of the test samples, it means that the lower the ratio of carbonyl BSA, the higher the action of reducing carbonyl protein is. The numerals in the table respectively show the ratios of carbonyl BSA when the test samples were respectively used alone against the measured value of carbonyl BSA, regarded as 1, for Control with no addition of any of the test samples.

TABLE 1

| Test sample | Ratio of carbonyl BSA |
| --- | --- |
| Control | 1 |
| Composition containing glycosyl hesperetin | 0.46 |
| Composition containing glycosyl naringenin | 0.77 |
| L-Ascorbic acid 2-glucoside | 0.73 |
| Niacinamide | 1.05 |
| Glutathione (reduced form) | 1.19 |

As clear from Table 1 and FIG. 1, when the ratio of carbonyl BSA of control was regarded as 1, the ratios of carbonyl BSA for the composition containing glycosyl hesperetin, the composition containing glycosyl naringenin, and the L-ascorbic acid 2-glucoside were respectively 0.46, 0.77, and 0.73, which were evidently lower than that of Control; revealing that the composition containing glycosyl hesperetin, the composition containing glycosyl naringenin, and the L-ascorbic acid 2-glucoside have an action of reducing carbonyl BSA, i.e., an action of reducing carbonyl protein. Among these, the composition containing glycosyl hesperetin was revealed to have the highest action of reducing carbonyl protein. While, the ratios of carbonyl BSA for niacinamide and glutathione (reducing form) were both higher than that of Control, revealing that they have no action of reducing carbonyl protein.

(5) Carbonyl Protein Reduction Test—1 (a Combination Test of a Composition Containing Glycosyl Hesperetin and Other Ingredients)

It was experimented a combination test of the composition containing glycosyl hesperetin, which showed the highest action of reducing carbonyl BSA, and the composition containing glycosyl naringenin or the L-ascorbic acid 2-glucoside, whose actions were inferior to that of the composition containing glycosyl hesperetin with the highest carbonyl BSA reduction action as found in the above (4). It was tested similarly as in the above (4), except for using the test solutions for carbonyl protein reduction test having a concentration of 0.1, 0.5, or 1.0 w/v % of the composition containing glycosyl hesperetin or the test solutions for carbonyl protein reduction test having a concentration of 0.1 w/v % of the composition containing glycosyl naringenin or the L-ascorbic acid 2-glucoside, in place of the test solution for carbonyl protein reduction test used in the above (4). The results are respectively in Tables 2 and 3 and FIGS. 2 and 3. The numerals with no symbol "%" in each table show ratios of carbonyl BSA obtained in such a manner of calculating the amount of carbonyl BSA for the system with either or both of the test samples that were respectively used alone or used in combination while regarding as one the amount of carbonyl BSA in each control system with no addition of any of the compositions containing glycosyl hesperetin or glycosyl naringenin.

TABLE 2

| | Ratio of carbonyl BSA Composition containing glycosyl naringenin | |
|---|---|---|
| Test sample | With no addition | Added in an amount of 0.1 w/v % |
| Control | 1 | 0.70 |
| Composition containing glycosyl hesperetin (0.1 w/v %) | 0.53 | 0.40 |
| Composition containing glycosyl hesperetin (0.5 w/v %) | 0.24 | 0.10 |
| Composition containing glycosyl hesperetin (1.0 w/v %) | 0.07 | 0.06 |

TABLE 3

| | Ratio of carbonyl BSA Composition containing L-ascorbic acid 2-glucoside | |
|---|---|---|
| Test sample | With no addition | Added in an amount of 0.1 w/v % |
| Control | 1 | 0.70 |
| Composition containing glycosyl hesperetin (0.1 w/v %) | 0.53 | 0.81 |
| Composition containing glycosyl hesperetin (0.5 w/v %) | 0.24 | 0.04 |
| Composition containing glycosyl hesperetin (1.0 w/v %) | 0.07 | 0.02 |

As clear from the results in Table 2 and FIG. 2, the combination use of the composition containing glycosyl hesperetin (0.1 w/v %) and the composition containing glycosyl naringenin (0.1 w/v %) marked a carbonyl BSA ratio of 0.40 that had been reduced from original 0.53 for the single use of the former composition. Similarly, the combination use of the composition containing glycosyl hesperetin (0.5 w/v % or 1.0 w/v %) and the composition containing glycosyl naringenin (0.1 w/v %) marked 0.10 or 0.06 that had been reduced from original 0.24 or 0.07, respectively, for the single use of the former composition. These results revealed that the combination use of the composition containing glycosyl hesperetin and the composition containing glycosyl naringenin enhances the action of reducing carbonyl BSA, i.e., the action of reducing carbonyl protein.

Further, as clear from the results in Table 3 and FIG. 3, the combination use of the composition containing glycosyl hesperetin (0.1 w/v %) and the L-ascorbic acid 2-glucoside (0.1 w/v %) increased from the original ratio of carbonyl BSA of 0.53 for the single use of the former composition to 0.81. Under the conditions, no carbonyl BSA reduction action was observed due to the combination use of the composition containing glycosyl hesperetin and the L-ascorbic acid 2-glucoside; however, the combination use of the composition containing glycosyl hesperetin (0.5 w/v % or 1.0 w/v %) and the L-ascorbic acid 2-glucoside (0.1 w/v %) reduced from the ratio of carbonyl BSA of 0.24 or 0.07 for the single use of the former composition to 0.04 or 0.02, respectively. These results revealed that the combination use of the composition of glycosyl hesperetin and the L-ascorbic acid 2-glucoside enhances the carbonyl BSA reducing action, i.e., the carbonyl protein reduction action exerted by the former composition.

All the findings, which were made based on the self-findings by the present inventors, are novel.

Although concrete data are not shown, any of the compositions containing glycosyl hesperetins in Examples 2 to 6 as shown below has a similar action as that of the composition containing glycosyl hesperetin used in this experiment.

(6) Carbonyl Protein Reduction Test—2 (a Combination Test of a Composition Containing Glycosyl Hesperetin and Any of Saccharides)

In the above (5), when the composition containing glycosyl hesperetin and the composition containing naringenin or the L-ascorbic acid 2-glucoside are used in combination, they acted cooperatively to show a carbonyl protein reduction action. Further, in this experiment, saccharides were focused on and tested as candidates for enhancing the carbonyl protein reduction action when used in combination with the composition containing glycosyl hesperetin.

Except for using any one of mannose, N-acetylglucosamine, "MALTOSE HHH" as a product name of maltose, raffinose, maltotetraose, and "TORNARE®" as a product name of glycosyl trehalose used as a cosmetic base material, which are shown in Table 4 below, in place of the composition containing glycosyl naringenin and the ascorbic acid 2-glucoside used in the above (4), and preparing it into a solution containing 0.1 w/v % of any of the above saccharide for use as a test solution for carbonyl protein reduction test, it was examined the carbonyl protein reduction action of the combination use the composition containing glycosyl hesperetin and any one of the above-identified saccharides similarly as in the above (4). The results are in Table 5.

TABLE 4

| Saccharide | Source |
|---|---|
| Mannose (a special grade reagent) | Wako Pure Chemical Industries Ltd., Osaka, Japan |
| N-Acetyl glucosamine (a special grade reagent) | Kishida Chemical Co., Ltd., Osaka, Japan |
| "MALTOSE HHH", a product name of maltose with a purity of at least 99% | Hayashibara Co., Ltd., Okayama, Japan |
| Raffinose (a special grade reagent) | Wako Pure Chemical Industries Ltd., Osaka, Japan |
| Maltotetraose | Wako Pure Chemical Industries Ltd., Osaka, Japan |
| "TORNARE ®", a product name of glycosyl trehalose as a cosmetic base material containing glycosyl trehalose as a main ingredient | Hayashibara Co., Ltd., Okayama, Japan |

TABLE 5

(Combination effect)

| | Control (No addition) | Composition containing glycosyl hesperetin (0.1 w/v %) | Combination use of a composition containing glycosyl hesperetin (0.1 w/v %) and any one of the saccharides below (0.1 w/v %) | | | | |
|---|---|---|---|---|---|---|---|
| | | | Mannose | N-Acetyl glucosamine | Maltose | Raffinose | Maltotetraose | Glycosyl trehalose |
| Ratio of carbonyl BSA | 1 | 0.51 | 1.3 | 0.79 | 0.11 | 0.54 | 0.13 | 0.13 |

(Reference: Effect of saccharide alone)

| | Control (No addition) | Single use of saccharide (0.1 w/v %) | | | | |
|---|---|---|---|---|---|---|
| | | Mannose | N-Acetyl glucosamine | Maltose | Raffinose | Maltotetraose | Glycosyl trehalose |
| Ratio of carbonyl BSA | 1 | 0.51 | 0.48 | 0.18 | 0.23 | 0.71 | 0.37 |

As clear from the results in Table 5, the single use of the composition containing glycosyl hesperetin distinctly reduced in its original ratio of carbonyl BSA from 0.51 to 0.11, 0.13, or 0.13 when the composition was used in combination with maltose, maltotetraose, or glycosyl trehalose, respectively. This result revealed that maltose, maltotetraose, and glycosyl trehalose have an action of distinctly enhancing the carbonyl BSA reducing action of the composition containing glycosyl hesperetin. While, it was revealed that maltose and raffinose in themselves have a carbonyl protein reduction action based on the fact that mannose, N-acetyl glucosamine, maltose, raffinose, maltotetraose, and glycosyl trehalose gave carbonyl BSA ratios of 0.51, 0.48, 0.18, 0.23, 0.71, and 0.37, respectively, when used alone. It was revealed that a single use of maltotetraose merely marked a carbonyl BSA ratio of 0.71; however, it gave a carbonyl BSA ratio of 0.13 (sharply reduced from 0.71) to exert a distinct carbonyl BSA reducing action, when used in combination with the composition containing glycosyl hesperetin.

(7) Carbonyl Protein Reduction Test—3 (a Combination Test of a Composition Containing Glycosyl Hesperetin and Other Organic Acids or Amino Acids)

This experiment was conducted with organic acids and amino acids, which were focused on as compounds to be used with the composition containing glycosyl hesperetin. Except for using a solution containing 0.05 w/v % of any one of lactic acid, tartaric acid, citric acid, salicylic acid, ferulic acid, glucuronic acid, glucuronolactone, acetic acid, sorbic acid, benzoic acid, glycine, and sodium glutamate as listed in Table 6, in place of the composition containing glycosyl naringenin or the L-ascorbic acid 2-glucoside used in the above (4), there was used as a test solution for carbonyl protein reduction test to examine the carbonyl protein reducing action of the combination use of the composition containing glycosyl hesperetin and any one of the above organic acids or the amino acids similarly as in the above (4). The results are in Table 7.

TABLE 6

| Organic acid and amino acid | Source |
|---|---|
| Lactic acid (for food additive) | Wako Pure Chemical Industries Ltd., Osaka, Japan |
| Tartaric acid (a special grade reagent) | Tokyo Chemical Industry Co., Ltd., Tokyo, Japan |
| Citric acid (a special grade reagent) | Wako Pure Chemical Industries Ltd., Osaka, Japan |
| Salicylic acid (a special grade reagent) | Wako Pure Chemical Industries Ltd., Osaka, Japan |
| Ferulic acid (with a purity of 99%) | Sigma-Aldrich, Japan, Tokyo, Japan |
| Glucuronic acid (a special grade reagent) | Wako Pure Chemical Industries Ltd., Osaka, Japan |
| Glucuronolactone (a special grade reagent) | Wako Pure Chemical Industries Ltd., Osaka, Japan |
| Acetic acid (for food additive) | KISHIDA CHEMICAL Co., Ltd, Osaka, Japan |
| Sorbic acid (a special grade reagent) | Wako Pure Chemical Industries Ltd., Osaka, Japan |
| Benzoic acid (a special grade reagent) | Wako Pure Chemical Industries Ltd., Osaka, Japan |
| Glycine (a special grade reagent) | Wako Pure Chemical Industries Ltd., Osaka, Japan |
| Sodium glutamate (a special grade reagent) | Wako Pure Chemical Industries Ltd., Osaka, Japan |

TABLE 7

(Combination effect)

Composition containing glycosyl hesperetin (0.1 w/v %) used in combination with any one of the following organic acids or amino acids (0.1 w/v %)

| | X | Y | A | B | C | D | E | F | G | H | I | J | K | L |
|---|---|---|---|---|---|---|---|---|---|---|---|---|---|---|
| Ratio of carbonyl BSA | 1 | 0.59 | 0.35 | 0.51 | 0.52 | 0.51 | 0.35 | 0.16 | 0.49 | 0.25 | 0.26 | 0.44 | 0.32 | 0.28 |

Note: The symbol "X" means control (No addition), while the symbol "Y" means a composition containing glycosyl hesperetin (0.1 w/v %). The symbols "A", "B", "C", "D", "E", "F", "G", "H", "I", "J", "K", and "L" mean lactic acid, tartaric acid, citric acid, salicylic acid, ferulic acid, glucuronic acid, glucuronolactone, acetic acid, sorbic acid, benzoic acid, glycine, and sodium glutamate, respectively.

(Reference: Effect of organic acid or amino acid when used alone)

Sole use of organic acid or amino acid (0.1 w/v %)

| | X | A | B | C | D | E | F | G | H | I | J | K | L |
|---|---|---|---|---|---|---|---|---|---|---|---|---|---|
| Ratio of carbonyl BSA | 1 | 0.89 | 0.95 | 0.96 | 1.02 | 0.82 | 1.01 | 1.07 | 1.08 | 1.04 | 0.95 | 0.71 | 0.77 |

Note: The symbol "X" means control (No addition). The symbols "A", "B", "C", "D", "E", "F", "G", "H", "I", "J", "K", and "L" mean lactic acid, tartaric acid, citric acid, salicylic acid, ferulic acid, glucuronic acid, glucuronolactone, acetic acid, sorbic acid, benzoic acid, glycine, and sodium glutamate, respectively.

As clear from the results in Table 7, it was revealed that the composition containing glycosyl hesperetin gave a ratio of carbonyl BSA of 0.59 when used alone, but the ratio was distinctly reduced to 0.35, 0.35, 0.16, 0.49, 0.25, 0.26, 0.44, 0.32, and 0.28 when used in combination with lactic acid, ferulic acid, glucuronic acid, glucuronolactone, acetic acid, sorbic acid, benzoic acid, glycine, or sodium glutamate. Thus, lactic acid, ferulic acid, glucuronic acid, glucuronolactone, acetic acid, sorbic acid, benzoic acid, glycine, and sodium glutamate were revealed to have an action of distinctly increasing the carbonyl BSA reducing action of a composition containing glycosyl hesperetin. Single use of any of the organic acids and the amino acids employed in this experiment gave a carbonyl BSA ratio ranging from 0.71 to 1.08 that were higher than that of the single use of the composition containing glycosyl hesperetin.

Based on the above-mentioned experimental results, the combination use of the composition containing glycosyl hesperetin and any one of L-ascorbic acid 2-glucoside, maltose, maltotetraose, glycosyl trehalose, lactic acid, ferulic acid, glucuronic acid, glucuronolactone, acetic acid, sorbic acid, benzoic acid, glycine, sodium glutamate, and a composition containing glycosyl naringenin cooperatively acts and exerts a distinct carbonyl protein reducing action compared to the single use of the composition containing glycosyl hesperetin. Particularly, when used in combination with maltotetraose, lactic acid, ferulic acid, glucuronic acid, glucuronolactone, acetic acid, sorbic acid, benzoic acid, glycine, or sodium glutamate, the composition containing glycosyl hesperetin exerts a significantly high carbonyl protein reducing action.

Although concrete data is not shown, any of the compositions containing glycosyl hesperetin disclosed in the later-mentioned Examples 2 to 6 exhibits the same action as the composition containing glycosyl hesperetin used in this experiment.

<Experiment 2: External Application Test on Human Skin—1>

(1) Summary

Since the composition containing glycosyl hesperetin was revealed to have a distinct carbonyl protein reducing action in the in vitro test conducted in Experiment 1, it was examined whether the effect of the composition on the already-generated carbonyl protein when practically applied to the skin externally.

(2) Application Test

Eleven healthy volunteers (seven men and four women), 24 to 38 years old, as subjects, were respectively allowed by themselves to apply the test solutions (pH 5.7) with the compositions shown in Table 8 to three sites on their upper arms opposite to their dominant arms, i.e., three inside skin parts (3 cm×3.5 cm) named test sites A, B, and C, respectively: By using cotton applicators, the test solutions were applied to the test site B of each subject twice a day (in the morning and in the evening after taking a bath) for seven days. On day eight after initiating the application test, the volunteers were subjected to tape stripping in such a manner of affixing "Corneum. Checker": AST-01, a tape for stripping corneum commercialized by Asahi Biomed, Co., Ltd., Tokyo, Japan, to each test site to collect corneum protein (called "corneum protein after completing the test", hereinafter). As a control, except for applying the control solution (pH 5.7) in Table 8 to the application site C, the above procedure was conducted to collect corneum protein (called "control corneum protein", hereinafter). As for the test site A, it was initially subjected to tape stripping using the tape for stripping corneum to collect corneum protein (called "corneum protein at initiating the test", hereinafter).

TABLE 8

| Ingredient | Control solution | Test solution |
|---|---|---|
| Glycerine | 2.2 g | 2.2 g |
| Butylene glycol (BG) | 2.0 g | 2.0 g |

TABLE 8-continued

| Ingredient | Control solution | Test solution |
|---|---|---|
| PEG-60 Hydrogenated castor oil | 0.2 g | 0.2 g |
| Polysorbate 20 | 0.2 g | 0.2 g |
| Methylparaben | 0.1 g | 0.1 g |
| Composition containing glycosyl hesperetin obtained in Example 1 | 0.0 g | 0.5 g |
| Citric acid | q.s. | q.s. |
| Potassium hydroxide | q.s. | q.s. |
| Refined water | q.s. | q.s. |
| Total | 100 g | 100 g |

<Evaluation Method>

The carbonyl protein reducing action was evaluated by quantifying the carbonyl protein as a causative substance for inducing skin yellowness in "corneum protein after completing the test" in the test site B applied with any of the test solutions and in "corneum protein at initiating the test" in the test site A, similarly as in the assay for the concentration of carbonyl BSA disclosed in "(2) Assay for reducing carbonyl protein (a sole use test). As a control, the carbonyl protein in the test site C applied with the control solution (called "control corneum protein") was quantified similarly as in the above.

The following were determined and statistically treated (one-sided t-test); for each subject, the difference between the level of carbonyl protein in "corneum protein after completing the test" in any of the test sites applied with any of the test solutions or in "control corneum protein" applied with the control solution and the level of carbonyl protein in "corneum protein at initiating the test", i.e., (Level of carbonyl protein in corneum protein after completing the test or the control corneum protein)−(Level of carbonyl protein in corneum protein at initiating the test)], and the ratio of (Level of carbonyl protein in corneum protein after completing the test)/(Level of carbonyl protein in corneum protein at initiating the test).

<Result>

FIGS. 4 and 5 are the results of the level of carbonyl protein (a causative substance for skin yellowness) in any of the test sites applied with any of the test solutions in each subject. As shown in FIG. 4, the subjects applied with the control solution increased in their carbonyl protein levels in corneum protein after completing the test, compared to those at initiating the test, meaning that the levels of carbonyl protein in the subjects' skins had increased during this experiment. On the contrary, the subjects applied with any of the test solutions reduced in carbonyl protein levels in corneum proteins after completing the test, compared to those at initiating the test. From FIG. 5, the subjects applied with the control solution increased in their carbonyl protein levels by about 1.1 times compared to those at initiating the test, while the subjects applied with any of the test solutions reduced in their carbonyl protein levels compared to those at initiating the test, meaning that the subjects with any of the test solutions distinctly, significantly reduced in carbonyl protein levels. This revealed that the application of the composition containing glycosyl hesperetin to the skin significantly reduces the already-generated carbonyl protein in the skin.

In spite of this experiment or an application test with only a short period of time of seven days, the fact that glycosyl hesperetin gave such a distinct, significant effect clearly shows that it distinctly, significantly, and effectively reduces the carbonyl protein already-formed in the skin. After completion of this experiment, since there was found no abnormality in the skin, etc., in every subject, due to this experiment, it can be judged that glycosyl hesperetin is a safe substance that can be successively, safely, and daily applied externally to humans. Any of other glycosyl hesperetins and hesperetins disclosed in the specification, as well as the compositions containing glycosyl hesperetins disclosed in the later disclosed Examples 2 to 6, have an action of reducing carbonyl protein already-formed in the skin, similarly as the composition containing glycosyl hesperetin used in this experiment.

This experiment revealed the fact that glycosyl hesperetin has an action of reducing carbonyl protein already-formed in the skin by using the healthy subjects, 24 to 38 years old. According to an experimental result conducted other than the experiment, the carbonyl protein reducing action exerted by glycosyl hesperetin is more distinctly observed in the elderly (not less than 40 years old) than the young generation. It is a truism that the application of glycosyl hesperetin to the elderly, who have a relatively high carbonyl protein level, shows a more distinct carbonyl protein reducing action exerted by the glycosyl hesperetin, considering that carbonyl protein, as a causative for skin yellowness, gradually accumulates in the skin to cause skin yellowness with ageing as the decrease in skin metabolism.

<Experiment 3: External Application Test on Humans—2>
(1) Summary

Following "External application test on humans—1" of Experiment 2, glycosyl hesperetin was examined for its effect on skin yellowness using the skin around subjects' eyes as an application site.

(2) Application Test

Sixteen females, who were 25 to 49 years old healthy subjects but were feeling stressed in daily life, were randomly divided into two groups (called groups A and B) consisting of eight subjects, and indicated to apply Cosmetic lotion A according to the present invention for use in Group A or Cosmetic lotion B as a control for use in Group B, which were composed of the composition shown in Table 9, to the test site twice a day (morning and evening, when any subject who takes a bath in the evening, she should apply Cosmetic lotion A or B after taking the bath) in such a manner of placing three milliliters of any of the cosmetic lotions per dose (called "application", hereinafter) and applying it to the prescribed site every day for eight weeks in total, followed by measuring their skin colors as indicated below before initiating the application, at four weeks before the application, and at eight weeks after the application to examine the effect of Cosmetic lotions A and B on skin yellowness. During the experiment, all the subjects were strictly allowed to avoid (a) physical stress such as scratching the test site, (b) excessive suntan, (c) excessive exercise, (d) taking any skin care other than Cosmetic lotions A and B, and (e) drinking on the eve of conducting the skin color measurement before initiating the application, at four weeks after initiating the application, and at eight weeks after initiating the application.

<Method of Judgement: Measurement of Color Difference (Skin-Color Measurement)>

Skin colors of the test sites were measured with "Konica Minolta's CM-2600d", a product name of a spectrophotometer or a color-difference meter, commercialized by Konica Minolta, Tokyo, Japan. The analysis objects were made "L* value" and "b* value" in L*a*b* color system, wherein L* value represents brightness and b* value is an indication of the degree of yellowness in the skin.

Among the eight subjects, two were dropped out during the experiment due to their personal circumstances, and therefore the data analysis of Group A was made based on the measurement results of six subjects, while that of Group B was made based on those of eight subjects. Tables 10 and 11 respectively show the measured value of L* value based on the color difference measurement (skin-color measurement) in the skin under each subject's eye and the variation ($\Delta L^*$ value) between the above each measured value and that at initiating the application to each subject. Tables 12 and 13 respectively show the measured value of b* value based on the color difference measurement in the skin under each subject's eye and the variation ($\Delta L^*$ value) between the above each measured value and that before initiating the application to each subject.

TABLE 9

| Ingredient | Cosmetic lotion A (Test solution) | Cosmetic lotion B (Control) |
|---|---|---|
| Glycerine | 2.2 | 2.2 |
| Butylene glycol (BG) | 2.0 | 2.0 |
| PEG-60 Hydrogenated castor oil | 0.2 | 0.2 |
| Polysorbate 20 | 0.2 | 0.2 |
| Composition containing glycosyl hesperetin obtained in Example 1 | 0.5 | 0 |
| Citric acid | q.s. | q.s. |
| Potassium hydroxide | q.s. | q.s. |
| Methylparaben | 0.1 | 0.1 |
| Purified water | q.s. | q.s. |
| Total | 100 | 100 |

In the table, the unit of numeral is gram.

TABLE 10

Change in L* value (the skin under each subject's eye, measured value)
L* Value

| Group with Cosmetic lotion A (n = 6) | | | | Group with Cosmetic lotion B (n = 8) | | | |
|---|---|---|---|---|---|---|---|
| Subject No. | X | Y | Z | Subject No. | X | Y | Z |
| 1 | 63.77 | 65.50 | 64.56 | 1 | 62.85 | 62.93 | 62.34 |
| 2 | 64.01 | 64.95 | 62.57 | 2 | 65.68 | 65.00 | 64.58 |
| 3 | 63.81 | 64.24 | 66.08 | 3 | 57.29 | 57.83 | 58.00 |
| 4 | 63.32 | 63.43 | 64.67 | 4 | 64.61 | 64.97 | 66.13 |
| 5 | 62.52 | 62.85 | 63.50 | 5 | 66.45 | 67.16 | 66.44 |
| 6 | 63.07 | 64.89 | 64.27 | 6 | 63.84 | 65.10 | 63.99 |
| | | | | 7 | 63.41 | 63.52 | 63.60 |
| | | | | 8 | 62.85 | 63.63 | 64.50 |
| Mean value | 63.42 | 64.31 | 64.27 | | 63.37 | 63.77 | 63.70 |
| Standard-deviation | 0.56 | 1.01 | 1.19 | | 2.78 | 2.73 | 2.65 |
| p[1] | | 0.030× | 0.150 | | | 0.093 | 0.360 |
| p[2] | | | | | 0.970 | 0.653 | 0.631 |

[1] Significant difference to the value before initiating the application (paired t-test)
[2] Significant difference to the value of the group with Cosmetic lotion A (student t-test)
× Significant increase in value
X: Before initiating the application
Y: Four weeks after initiating the application
Z: Eight weeks after initiating the application

TABLE 11

Change in L* value (the skin under each subject's eye, variation between before and after initiating the application)
$\Delta L^*$ Value

| Group with Cosmetic lotion A (n = 6) | | | | Group with Cosmetic lotion B (n = 8) | | | |
|---|---|---|---|---|---|---|---|
| Subject No. | X | Y | Z | Subject No. | X | Y | Z |
| 1 | 0.00 | 1.73 | 0.79 | 1 | 0.00 | 0.09 | −0.51 |
| 2 | 0.00 | 0.95 | −1.44 | 2 | 0.00 | −0.68 | −1.10 |
| 3 | 0.00 | 0.43 | 2.27 | 3 | 0.00 | 0.55 | 0.72 |
| 4 | 0.00 | 0.12 | 1.35 | 4 | 0.00 | 0.36 | 1.51 |
| 5 | 0.00 | 0.34 | 0.98 | 5 | 0.00 | 0.71 | −0.01 |

TABLE 11-continued

Change in L* value (the skin under each subject's eye, variation between before and after initiating the application)
ΔL* Value

| Group with Cosmetic lotion A (n = 6) | | | | Group with Cosmetic lotion B (n = 8) | | | |
|---|---|---|---|---|---|---|---|
| Subject No. | X | Y | Z | Subject No. | X | Y | Z |
| 6 | 0.00 | 1.82 | 1.20 | 6 | 0.00 | 1.26 | 0.15 |
|  |  |  |  | 7 | 0.00 | 0.11 | 0.19 |
|  |  |  |  | 8 | 0.00 | 0.78 | 1.65 |
| Mean value | 0.00 | 0.90 | 0.86 |  | 0.00 | 0.40 | 0.33 |
| Standard-deviation | 0.00 | 0.73 | 1.24 |  | 0.00 | 0.58 | 0.94 |
| p[1] |  | 0.030[✕] | 0.150 |  |  | 0.093 | 0.360 |
| p[2] |  |  |  |  |  | 0.179 | 0.377 |

[1] Significant difference to the value before initiating the application (paired t-test)
[2] Significant difference to the value of the group with Cosmetic lotion A (student t-test)
[✕] Significant increase in value
X: Before initiating the application
Y: Four weeks after initiating the application
Z: Eight weeks after initiating the application

TABLE 12

Change in L* value (the skin under each subject's eye, measured value)
b* Value

| Group with Cosmetic lotion A (n = 6) | | | | Group with Cosmetic lotion B (n = 8) | | | |
|---|---|---|---|---|---|---|---|
| Subject No. | X | Y | Z | Subject No. | X | Y | Z |
| 1 | 17.38 | 17.65 | 17.05 | 1 | 16.06 | 15.42 | 14.96 |
| 2 | 17.71 | 16.98 | 16.77 | 2 | 16.07 | 15.37 | 15.57 |
| 3 | 18.18 | 17.06 | 16.69 | 3 | 16.77 | 17.59 | 17.29 |
| 4 | 18.87 | 17.99 | 19.07 | 4 | 17.01 | 16.10 | 16.06 |
| 5 | 19.03 | 17.92 | 17.66 | 5 | 17.07 | 16.63 | 16.30 |
| 6 | 19.27 | 19.42 | 18.96 | 6 | 17.25 | 16.97 | 18.38 |
|  |  |  |  | 7 | 18.50 | 18.36 | 19.52 |
|  |  |  |  | 8 | 19.88 | 19.79 | 19.91 |
| Mean value | 18.41 | 17.84 | 17.70 |  | 17.33 | 17.03 | 17.25 |
| Standard-deviation | 0.77 | 0.88 | 1.07 |  | 1.28 | 1.52 | 1.85 |
| p[1] |  | 0.076 | 0.049[✕] |  |  | 0.156 | 0.804 |
| p[2] |  |  |  |  | 0.095 | 0.270 | 0.603 |

[1] Significant difference to the value before initiating the application (paired t-test)
[2] Significant difference to the value of the group with Cosmetic lotion A (student t-test)
[✕] Significant reduction in value
X: Before initiating the application
Y: Four weeks after initiating the application
Z: Eight weeks after initiating the application

TABLE 13

Change in b* value (the skin under each subject's eye, variation between before and after initiating the application)
Δb* Value

| Group with Cosmetic lotion A (n = 6) | | | | Group with Cosmetic lotion B (n = 8) | | | |
|---|---|---|---|---|---|---|---|
| Subject No. | X | Y | Z | Subject No. | X | Y | Z |
| 1 | 0.00 | 0.28 | −0.32 | 1 | 0.00 | −0.64 | −1.11 |
| 2 | 0.00 | −0.74 | −0.94 | 2 | 0.00 | −0.70 | −0.51 |
| 3 | 0.00 | −1.12 | −1.48 | 3 | 0.00 | 0.81 | 0.52 |
| 4 | 0.00 | −0.88 | 0.20 | 4 | 0.00 | −0.91 | −0.95 |
| 5 | 0.00 | −1.11 | −1.37 | 5 | 0.00 | −0.44 | −0.77 |
| 6 | 0.00 | 0.15 | −0.31 | 6 | 0.00 | −0.28 | 1.12 |
|  |  |  |  | 7 | 0.00 | −0.14 | 1.02 |
|  |  |  |  | 8 | 0.00 | −0.09 | 0.03 |

TABLE 13-continued

Change in b* value (the skin under each subject's eye, variation between before and after initiating the application)
Δb* Value

| Group with Cosmetic lotion A (n = 6) | | | | Group with Cosmetic lotion B (n = 8) | | | |
|---|---|---|---|---|---|---|---|
| Subject No. | X | Y | Z | Subject No. | X | Y | Z |
| Mean value | 0.00 | −0.57 | −0.70 | | 0.00 | −0.30 | −0.08 |
| Standard-deviation | 0.00 | 0.62 | 0.67 | | 0.00 | 0.53 | 0.89 |
| p[1] | | 0.076 | 0.049✕ | | | 0.156 | 0.804 |
| p[2] | | | | | | 0.398 | 0.176 |

[1] Significant difference to the value before initiating the application (paired t-test)
[2] Significant difference to the value of the group with Cosmetic lotion A (student t-test)
✕ Significant reduction in value
X: Before initiating the application
Y: Four weeks after initiating the application
Z: Eight weeks after initiating the application <Result>

As shown in Table 10, the mean value of the L* values of the skins under all of the subjects' eyes with Cosmetic lotion B as control was 63.37 before initiating the application, and it turned into 63.77 at four weeks after initiating the application and 63.70 at eight weeks after the initiation, wherein there was found no substantial change in the L* value. While, the mean values of the L* values of the skins under all of the subjects' eyes with Cosmetic lotion A containing glycosyl hesperetin was 63.42 before initiating the application, and it turned into 64.31 at four weeks after initiating the application, and 64.27 at eight weeks after the initiation, which were clearly higher than those of their L* values before initiating the application. Also, as shown in Table 11, the variations of the L* values (ΔL* values) of the subjects with Cosmetic lotion B as control were 0.40 and 0.33 at four weeks and eight weeks after initiating the application, respectively, based on the standard value "0" before initiating the application. On the contrary, the ΔL* values of the subjects with Cosmetic lotion A according to the present invention were 0.90 and 0.86 at four weeks and eight weeks after initiating the application, respectively, based on the standard value "0" before initiating the application. Accordingly, the ΔL* values, i.e., 0.90 and 0.86, of the subjects with the above Cosmetic lotion A were as high as at least about two times higher than those of 0.40 and 0.33, of the subjects with Cosmetic lotion B as control. Considering the fact that the L* value is an index for skin brightness, Cosmetic lotion A incorporated with the composition containing glycosyl hesperetin according to the present invention was revealed to have an action of effectively improving the brightness of the skin.

As shown in Table 12, the b* values of the skins under all of the subjects' eyes with Cosmetic lotion B as control before initiating the application, at four weeks after initiating the application, and at eight weeks after initiating the application were respectively 17.33, 17.03, and 17.25, indicating that there was no substantial change in the b* values before and after initiating the application. On the contrary, the mean value of the b* values of the skins under all of the subjects' eyes with Cosmetic lotion A containing glycosyl hesperetin according to the present invention distinctly reduced from 18.41 before initiating the application to 17.84 and 17.70 at four weeks and eight weeks after initiating the application, respectively. As shown in Table 13, the reduction degree was as follows: the mean values of the variations of the b* values (Δb* values) of the subjects with Cosmetic lotion B as control were −0.30 and −0.08, while those for the subjects with Cosmetic lotion A incorporated with the composition containing glycosyl hesperetin according to the present invention were −0.57 and −0.70 at four weeks and eight weeks after initiating the application, respectively. Thus, the variations of the Δb* values of the subjects with Cosmetic lotion A increased by about two times and about nine times at four and eight weeks after initiating the application, respectively, compared to those of the subjects with Cosmetic lotion B as control. Accordingly, Cosmetic lotion A was revealed to have an action of quite distinctly improving skin yellowness.

From the experimental result, since the composition of reducing skin yellowness of the present invention distinctly reduces the b* value as an index for skin yellowness and improves the L* value as an index for skin brightness, the composition improves skin yellowness and makes the skin to be transparent and to have healthy tone. The action of improving skin yellowness exerted by the external dermal agent for reducing skin yellowness according to the present invention tended to be more distinctly observed in subjects with an increased skin yellowness before initiating the application of the external dermal agent.

<Experiment 4: Physical Property of Glycosyl Hesperetin>

The following were used as glycosyl hesperetins: four different types of pulverized glycosyl hesperetins (Test samples 1 to 4) that were similarly prepared by the methods in the later disclosed Examples 2, 4, 5, and 6, except for not using any reducing agent; and four different types of pulverized glycosyl hesperetins (Test samples 5 to 8) that were similarly prepared by the method in Example 2, except for using as a reducing agent 0.1, 0.09, 0.07, or 0.04% of sodium metabisulfite. Test sample 1, which was prepared without using any of the prescribed reducing agents, is a similar product to the pulverized glycosyl hesperetin obtained in Example 1 because it contained α-glucosyl hesperidin, hesperidin, and other ingredients in amounts substantially equal to those of the above pulverized glycosyl hesperetin.

(1) Furfural Content

Test samples 1 to 8 were respectively quantified their furfural contents by the following protocols and apparatuses:

<A. Sample Preparation>

(a) A half gram of glycosyl hesperetin as a test sample was placed in a 50 mL stoppered Erlenmeyer flask.
(b) To the flask were added 5.0 mL of ionized water to dissolve the glycosyl hesperetin and 20 μL of 0.0025% of cyclohexanol as a surrogate substance (an index for determining the yield of the test sample upon the analysis).

(c) To the resulting mixture were added 1.5 g of sodium chloride and 3 mL of diethyl ether, followed by mixing the resulting mixture at 700 rpm for 10 min.

(d) All the resulting mixture was transferred to a separatory funnel and allowed to stand for 10 min, followed by collecting the diethyl ether layer, dehydrating the resulting solution with sodium sulfate, and concentrating the resultant up to give a volume of about 200 µL under a nitrogen-gas stream.

(e) The concentrate was sampled in one microliter and subjected to GC/MS analyzer.

(f) As a control, except for using a reagent grade furfural in place of the glycosyl hesperetin, it was treated with the protocols (a) to (e) similarly as in the test sample.

<GC/MS Analysis Conditions>

GC/MS Analyzer: "Clarus 680 GC" and "Clarus SQ8T GC/MS", both commercialized by PerkinElmer, Inc., MA, USA.

Column: VF-WAXms, having a length of 30 m, an inner diameter of 0.25 mm, and a membrane thickness of 0.25 µm, commercialized by Agilent Technologies Inc., CA, USA.

Detector: mass analyzer

Carrier gas: helium gas

Linear velocity: 35 cm/sec

Increasing temperature conditions: Keeping the column temperature at 40° C. for three minutes, increasing the column temperature from 40° C. to 80° C. at a rate of 5° C./min, increasing the column temperature from 80° C. to 200° C. at a rate of 10° C./min, keeping the column temperature at 200° C. for seven minutes, increasing the column temperature from 200° C. to 220° C. at a rate of 10° C./min, and then keeping the column temperature at 220° C. for eight minutes.

Surrogate substance: cyclohexanol

Internal standard substance: heneicosane

Extraction solvent: diethyl ether

<B. Quantification of Furfural in Sample>

A calibration curve was drawn with the data on furfural, as a control, a special grade reagent, commercialized by Wako Pure Chemical Industries, Ltd., Osaka, Japan, determined by GC/MS analysis; based on this, test samples were determined for furfural contents.

(2) 4-VA Content

The test samples 1 to 8 were respectively determined for 4-VA contents using the following reagents, protocols, and apparatuses. The measurement was conducted in accordance with "About benzene in soft drinks" of Notification No. 0728008, as of Jul. 28, 2006, issued by the First Evaluation and Registration Division Chief, Department of Food Safety, Standards and Evaluation Division, Pharmaceutical and Food Safety Bureau, Organization of the Ministry of Health, Labour and Welfare, Tokyo, Japan.

<A. Reagents and Solutions Prepared Therewith>

(a) Sodium chloride, a specimen for water quality test, commercialized by Wako Pure Chemical Industries, Ltd., Osaka, Japan.

(b) Preparation of Cyclohexanol Standard Stock Solution

Cyclohexanol, a first-grade reagent, commercialized Katayama Chemical Industries, Co., Ltd., Osaka, Japan, was dissolved in methanol of Japanese Pharmacopoeia (JP) for use in general tests into 0.01 w/w % cyclohexanol solution (called "cyclohexanol standard stock solution", hereinafter).

(c) Internal Standard Solution

Using the above cyclohexanol standard stock solution and methanol, 0.0004 w/w % cyclohexanol solution (called "internal standard solution 1", hereinafter) and 0.00004 w/w % cyclohexanol solution (called "internal standard solution 2", hereinafter) were prepared.

(d) Preparation of Standard Stock Solution

4-VA, commercialized by Wako Pure Chemical Industries, Ltd., Osaka, Japan, was dissolved in methanol into 0.0005 w/w % 4-VA solution (called "standard solution A", hereinafter) or 0.00005 w/w % 4-VA solution (called "standard solution B", hereinafter).

(e) Preparation of Standard Stock Solution for Calibration Curve

Five different standard-stock-mixture solutions for calibration curve, having respective 4-VA concentrations of 0.05, 0.1, 0.2, 0.5, and 1.0 µg/mL, were prepared using the above standard solutions A and B, the above internal standard solution 1, and methanol.

(f) Preparation of Standard Solution for Calibration Curve

Five different standard solutions for calibration curve were prepared as follows: Ten milliliter aliquots of ultrapure water were placed in five 20-mL headspace vials, added with 10 µL of any one of the above five different standard-stock-mixture solutions for calibration curve, and added with 3.0 g of sodium chloride, followed by immediately sealing the vials and stirring the solutions in the vials to dissolve the contents therein.

<B. Preparation of Test Sample>

The test samples 1 to 8 were respectively, precisely weighed by 0.20 g, d.s.b., placed in eight 20-mL headspace vials, added with ultrapure water to give a total net weight of 10.0 g in each vial, and dissolved therein by stirring. To each of the resulting aqueous solutions were added 10 µL of the above internal standard solution 2 and 3.0 g of sodium chloride, followed by immediately sealing the vials, dissolving the contents in the vials by stirring to obtain eight different types of test samples containing any one of the test samples 1 to 8.

<C. Quantitative Method for 4-VA>

(a) Measurement Conditions

<GC/MS Analysis Conditions>

GC/MS analyzer: "Clarus SQ8T GC/MS", commercialized by PerkinElmer, Inc., MA, USA.

Head space sampler: "TurboMatrix Trap 40", commercialized by PerkinElmer, Inc., MA, USA.

Column: VF-WAXms, having a column length of 30 m, an inner diameter of 0.25 mm, and a membrane thickness of 0.25 µm, commercialized by Agilent Technologies Inc., CA, USA.

Detector: mass analyzer

Carrier gas: helium gas

Linear velocity: 35 cm/sec

Column injection temperature: 200° C.

Increasing temperature conditions: Keeping the column temperature at 40° C. for three minutes, increasing the column temperature from 40° C. to 80° C. at a rate of 5° C./min, increasing the column temperature from 80° C. to 200° C. at a rate of 10° C./min, keeping the column temperature at 200° C. for seven minutes, increasing the column temperature from 200° C. to 220° C. at a rate of 10° C./min, and then keeping the column temperature at 220° C. for eight minutes.

Vial oven temperature: 60° C.

Needle temperature: 140° C.

Transfer line temperature: 205° C.

Vial-heating time: 30 min

<Detection Method>
  Ionization (Electron impact (EI)) method
  Selected ion monitoring (SIM)
  m/z 134, 119 (4-VA)
  m/z 82, 57 (cyclohexanol, a first-grade reagent, commercialized by Katayama
  Chemical Industries Co., Ltd, Osaka, Japan)
(b) Quantification of 4-VA Based on the ratio of the peak heights of 4-VA and cyclohexanol, as an internal standard, for the above eight test samples and the five standard mixture solutions for generating a calibration curve, as well as on a separately created 4-VA calibration curve, the test samples 1 to 8 were determined for their 4-VA concentrations to calculate their 4-VA contents.

(3) Color Tone and Coloration Degree

The test samples 1 to 8 in aqueous solution forms were respectively, macroscopically observed their color tones and determined for coloration degrees by the following procedures: The test samples 1 to 8 were respectively prepared into 1 w/w % aqueous solutions, and 40 mL of each of which was placed in a 50-mL sealed container and heated at 100° C. for 30 min. Thereafter, each of the resulting solutions was adjusted to 27° C., placed in a cuvette with 1-cm width, and measured for absorbances of $OD_{420\ nm}$ and $OD_{720\ nm}$ at wavelengths of 420 nm and 720 nm using "UV-2600", a product name of a spectrophotometer, commercialized by Shimadzu Corporation, Kyoto, Japan, followed by determining the difference between the two absorbances ($OD_{420\ nm}-OD_{720\ nm}$) for use as a coloration degree, where the smaller the difference between the two absorbances, the lower the coloration degree is.

elements by the following procedure as a facile method: Each of the test samples 1 to 8 was precisely weighed by about 0.5 g in "Falcon Tube", a product name of a 50-mL container, commercialized by Japan, Becton Dickinson and Company, Tokyo, Japan, added with and dissolved in 20 mL of ultrapure water by heating, added with 0.54 mL of 60 w/w % aqueous nitric acid solution for precision assay, heated at 70° C. for 14 hours, cooled to ambient temperature, adjusted to give a total volume of 50 mL with ultrapure water, and quantified for metal elements using the following analyzer under the conditions below. As a control, a sample consisting of ultrapure water was used.

<Apparatus and Measurement Conditions>

Inductively coupled plasma emission spectrophotometer: "CIROS-120", commercialized by SPECTRO Analytical Instruments GmbH, Boschstrasse, Germany Plasma power: 1,400 W Plasma gas (Ar): 13.0 L/min Auxiliary gas (Ar): 1.0 L/min Nebulizer gas (Ar): 1.0 L/min Pump operation: 1.0 mL/min Method of calculating the content of metal elements (ppm): {(Measured value of a test sample)−(Measured value of Control)}×Dilution rate Table 14 shows the results of the above items (1) to (5). Since the compositions of the glycosyl hesperetins of the test samples 1 to 8 were substantially the same as those disclosed in Examples 1, 3, 4, or 5, they were omitted from Table 14.

TABLE 14

| | Test sample | Furfural content (ppb) | 4-VA Content (ppb) | Color tone | Coloration degree ($OD_{420\ nm}-OD_{720\ nm}$) | Electric conductivity (µs/cm) | Content of metal element (ppm) | | | |
|---|---|---|---|---|---|---|---|---|---|---|
| | | | | | | | Ca | K | Mg | Na |
| Product without treatment with any reducing agent | 1* | 308 | 40.2 | Pale yellow | 0.24 | 10.59 | 2.948 | 0.172 | 0.464 | 0.975 |
| | 2 | 322 | 46.6 | Pale yellow | 0.26 | 11.77 | 3.038 | 0.186 | 0.560 | 1.175 |
| | 3 | 343 | 55.1 | Pale yellow | 0.26 | 10.94 | 3.248 | 0.192 | 0.564 | 1.205 |
| | 4 | 385 | 63.8 | Pale yellow | 0.26 | 11.46 | 4.538 | 0.242 | 0.732 | 1.205 |
| Product treated with reducing agent | 5 | 8 | 1.2 | Pale yellow** | 0.15 | 2.86 | 0.374 | 0.039 | 0.052 | 0.072 |
| | 6 | 10 | 1.5 | Pale yellow** | 0.17 | 4.54 | 0.385 | 0.042 | 0.063 | 0.088 |
| | 7 | 11 | 1.8 | Pale yellow** | 0.20 | 6.19 | 0.400 | 0.043 | 0.063 | 0.087 |
| | 8 | 12 | 2.1 | Pale yellow** | 0.20 | 6.59 | 0.455 | 0.050 | 0.077 | 0.092 |

Note:
The symbol "*" means that it is substantially the same as conventional glycosyl hesperetin prepared by the method in Example 1.
The symbol "**" means that it has a more pale yellow color tone than those of the test samples 1 to 4 as products without treatment with any reducing agent.

(4) Electric Conductivity

The test samples 1 to 8 were respectively dissolved in refined water into 1 w/v % aqueous solutions, which were then respectively heated at 100° C. for 30 min in a sealed container, cooled to 20° C., and measured for electric conductivity at 20° C. using "CM-50AT", a product name of a conductance meter, commercialized by DKK Toa Corporation, Tokyo, Japan.

(5) Content of Ionic Compound

Since ionic compounds could not be easily quantified, they were quantified based on the contents of cationic metal As clear from Table 14, the furfural contents in the test samples 1 to 4 were all over 300 ppb, while those in the test samples 5 to 8 were all about 10 ppb. The 4-VA contents in the test samples 1 to 4 were all over 40 ppb, while those in the test samples 5 to 8 were all about 2 ppb or lower.

As shown in Table 14, the test samples 1 to 4, as products without treatment with any reducing agent, were macroscopically observed to show color tones of pale yellow in aqueous solution forms; while the test samples 5 to 8, as products treated with reducing agent, gave apparently more pale color tones in aqueous solution forms, compared with those of the test samples 1 to 4. When determined with a spectrophotometer, all of the test samples 1 to 4 in aqueous solution forms gave coloration degrees of 0.24 or higher, while those of the test samples 5 to 8 in aqueous solution forms were as low as 0.20 or lower. The more of the amount of a reducing agent used, the lower the coloration degrees of the test samples 5 to 8 became.

As clear from Table 14, the test samples 1 to 4 in aqueous solution forms had electric conductivities of about 11 to about 12 µS/cm as being over 10 µS/cm, while the test samples 5 to 8 in aqueous solution forms had electric conductivities of about 3 to about 7 µS/cm as being below 10 µS/cm.

Besides, as clear from Table 14, any one of the contents of calcium, potassium, magnesium, and sodium as metal elements in the test samples 5 to 8 were evidently low compared with those of the test samples 1 to 4, and these results were well coincided with the results of their measured electric conductivities.

These results revealed that, compared with products without treatment with any reducing agent, products treated with reducing agents were significantly reduced in furfural content, and also distinctly lowered in 4-VA content, coloration degree, electric conductivity, and metal element content.

<Experiment 5: Relationship Between the Miscellaneous Tastes and Coloration of Glycosyl Hesperetin and the Furfural and 4-VA Contents Thereof>

The following experiment was conducted to examine the relationship between the miscellaneous tastes and coloration of glycosyl hesperetin and the furfural and 4-VA contents thereof.

(1) Preparation of Test Samples

In accordance with the methods in the later disclosed Example 5 and Example 1, there were provided a glycosyl hesperetin as a product treated with a reducing agent (called "Sample A", hereinafter) and another sample as a product without treatment with any reducing agent (called "Sample B", hereinafter). For convenience, Samples A and B were mixed in appropriate ratios to obtain three types of glycosyl hesperetin samples with stepwisely different furfural contents (called "test samples 9 to 11") as shown in Table 16.

(2) Contents of Furfural and 4-VA

The contents of furfural and 4-VA in the test samples 9 to 11 were respectively determined according to the measurement methods shown in the items of "(1) Furfural content" and "(2) 4-VA Content" in Experiment 4.

(3) Test on Coloration Judgement

Nine healthy females and males, consisting of two females and seven males, 28 to 57 years old, as panelists, were subjected to an evaluation test on coloration using the test samples 9 to 11 and sample B (called "Control", hereinafter). These test samples 9 to 11 and Control were respectively dissolved in distilled water at ambient temperature into 1 w/w % aqueous solutions, which were then macroscopically observed and judged by the panelists as follows: It was judged as "Judgement A1", when the solution(s) was/were evaluated and judged by the panelists as "being reduced in coloration" compared with Control; and it was judged as "Judgement B1", when the solution(s) was/were evaluated and judged as "being reduced in coloration" compared with Control. The results are in Table 15.

(4) Sensory Test

The above nine females and males as panelists were subjected to a sensory test on the miscellaneous tastes of the aforesaid test samples 9 to 11 and Control. These test samples 9 to 11 and Control were respectively dissolved in distilled water at ambient temperature into 1 w/w % aqueous solutions, which were then tasted by the panelists, followed by allowing the panelists to judge the test samples 9 to 11 as follows: It was judged as "Judgement A2" when the aqueous solution(s) was/were evaluated as "being improved in miscellaneous tastes", compared with Control; and it was judged as "Judgement B2" when the solution(s) was/were evaluated as "being not improved in miscellaneous tastes", compared with Control. The results are in Table 15.

TABLE 15

| | | | Number of panelists | | | |
| | | | Test on coloration | | Sensory test | |
| Test sample | Furfural content (ppb) | 4-VA content (ppb) | Judgement A1 | Judgement B1 | Judgement A2 | Judgement B2 |
|---|---|---|---|---|---|---|
| Sample B (Control) | 330 | 45.0 | | | | |
| 9 | 234 | 39.4 | 4 | 5 | 4 | 5 |
| 10 | 171 | 29.1 | 9 | 0 | 8 | 1 |
| 11 | 108 | 10.2 | 9 | 0 | 9 | 0 |
| Sample A | 56 | 2.0 | | | | |

Note:
In the table, "Judgement A1" and "Judgement B1" mean that, in the test on coloration judgement, each panelist evaluated a test sample as "being reduced in coloration" and "being not reduced in coloration" compared with Control, respectively. While, "Judgement A2" and "Judgement B2" mean that, in the sensory test, each panelist evaluated a test sample as "being improved in miscellaneous tastes" and "being not improved in miscellaneous tastes" compared with Control, respectively.

As clear from the results in Table 15, the miscellaneous tastes of glycosyl hesperetins were significantly and distinctly improved at the furfural content of around 200 ppb as a border, and they were significantly and distinctly improved at the 4-VA content of around 30 ppb as a border. The same applied to the coloration of glycosyl hesperetins.

These results revealed that glycosyl hesperetins with a furfural content of less than 200 ppb and a 4-VA content of not higher than 30 ppb are the ones that are significantly reduced in miscellaneous tastes compared with conventional products. In other words, it was revealed that the furfural content and the 4-VA content can be made as indices for surely distinguishing glycosyl hesperetins that are significantly reduced in miscellaneous tastes and distinctly reduced in coloration. The glycosyl hesperetins according to the present invention can be easily obtained by using a glycosyl hesperetin with a furfural content of less than 200 ppb and a 4-VA content of not higher than 30 ppb as an index.

Incidentally, the following Tables 14 and 16 are respectively the results of the above Experiment 4 and the summary of the relationship between the miscellaneous tastes of particulate compositions containing glycosyl hesperetins and the furfural and 4-VA contents thereof disclosed in the later described Examples 1 to 8. In Table 16, the test samples 5 to 8 as products treated with reducing agents and the pulverized compositions containing glycosyl hesperetins in Examples 2 to 8 (called "samples treated with reducing agents" all together, hereinafter) had furfural contents of not higher than 191 ppb and 4-VA contents of not higher than 28.7 ppb, meaning that the products treated with reducing agents were significantly reduced in the miscellaneous tastes as a characteristic of products without treatment with any reducing agent. On the contrary, the test samples 1 to 5, i.e., particulate glycosyl hesperetins, as products without treatment with any reducing agent (called "samples without treatment with any reducing agent" all together, hereinafter) had furfural contents of 308 ppb or more and 4-VA contents of 40.0 ppb or more, and they all had miscellaneous tastes characteristic of products without treatment with any reducing agent.

The results in Table 16 below are well coincided with those in Experiment 4. Based on these results, it can be judged that glycosyl hesperetins, which have furfural contents of less than 200 ppb and/or 4-VA contents of less than 30 ppb, can be selected by using the furfural content and/or the 4-VA content, as indices, to obtain the desired glycosyl hesperetins that are significantly reduced in miscellaneous tastes, compared to products without treatment with any reducing agent.

TABLE 16

| Test samples | | Furfural content (ppb) | 4-VA Content (ppb) | Miscellaneous tastes |
|---|---|---|---|---|
| Samples without treatment with any reducing agent | 1* | 308 | 40.2 | x |
| | 2* | 322 | 46.6 | x |
| | 3* | 343 | 55.1 | x |
| | 4* | 385 | 63.8 | x |
| | 5 (Example 1) | 310 | 40.0 | x |
| Samples treated with reducing agent | Example 8 | 191 | 28.7 | ○ |
| | Example 7 | 180 | 20.0 | ○ |
| | 8* | 12 | 2.1 | ○ |
| | Example 2 | 12 | 2.0 | ○ |
| | 7* | 11 | 1.8 | ○ |
| | Example 3 | 11 | 1.5 | ○ |
| | Example 4 | 10 | 3.0 | ○ |
| | 6* | 10 | 1.5 | ○ |
| | Example 6 | 10 | 1.5 | ○ |
| | Example 5 | 9 | 2.0 | ○ |
| | 5* | 8 | 1.2 | ○ |

Note:
In the table, the test samples affixed with the symbol "*" are cited from Table 14 in the specification.
Those with the symbols "○" and "x" mean that they are reduced in miscellaneous tastes as a characteristic of products without treatment with any reducing agent and that they have substantially the same level of miscellaneous tastes as those of the products, respectively.

The results in Table 16 revealed that glycosyl hesperetins as products treated with reducing agents are significantly reduced in miscellaneous tastes and distinctly reduced in coloration and unpleasant odor, compared to glycosyl hesperetins without treatment with any reducing agent; thus, they can be arbitrarily incorporated into the external dermal agent for reducing skin yellowness of the present invention.

<Experiment 6: Sensory Test>

(1) Preparation of Test Sample

A sensory test shown in the following item (2) was performed with eight healthy panelists, consisting of two females and six males, 28 to 59 years old, by using both of the test sample 6, which gave an intermediate value of each of furfural content, coloration degree, electric conductivity, and metal element content, among the test samples 5 to 8 as products treated with reducing agents used in Experiment 4; and the test sample 1, which gave the minimum value for each of furfural content, coloration degree, electric conductivity, and metal element content, among the test samples 1 to 4 as products treated with reducing agents used in Experiment. The test sample 1 as a product without treatment with any reducing agent and the test sample 6 as a product treated with reducing agent were respectively dissolved at ambient temperature in RO water, obtained through a reverse osmosis membrane, to obtain 1% w/v aqueous solutions for use as unheated samples of the test samples 1 and 6, respectively, which were then stored in sealed containers until being subjected to the following test. While, the test samples 1 and 6 without heat treatment were respectively placed in a container, sealed therein, heated in a boiling water bath for 30 min, and cooled to an ambient temperature to obtain heated test samples 1 and 6.

(2) Sensory Test

Before tasting, each panelist was asked to individually evaluate (a) coloration and (b) odor of 10-mL aliquots of the unheated test samples 1 and 6 and the heated test samples 1 and 6, all of which had been obtained in the above evaluation item (1) and adjusted to an ambient temperature. Thereafter, each panelist was allowed to gargle with plain boiled water before tasting each test sample and allowed to individually evaluate (c) bitterness (including roughness, harshness, or astringency), (d) aftertaste, and (e) odor when tasting. The evaluation standard for the above items is shown in Table 17 below. Each panelist was allowed to evaluate the unheated or heated test sample 6 in terms of the above evaluation items (a) to (e), where the unheated test sample 6 and the heated test sample 6 were evaluated with, as controls, the unheated test sample and the heated test sample 1, respectively. The results are respectively in Tables 18 and 19.

Evaluation Standard:

TABLE 17

| | | | Evaluation score (judged on 5-point evaluation scale) |
|---|---|---|---|
| Before tasting | (a) Coloration | Comparison to products without treatment with any reducing agent | 1: Distinctly low<br>2: Slightly low<br>3: Comparable<br>4: Slightly high<br>5: Distinctly high |
| | (b) Odor | Comparison to products without treatment with any reducing agent | 1: Distinctly weak<br>2: Slightly weak<br>3: Comparable<br>4: Slightly sharp<br>5: Distinctly sharp |
| When tasting | (c) Bitterness | Comparison to products without treatment with any reducing agent | 1: Distinctly preferable<br>2: Slightly preferable<br>3: Undecided<br>4: Rather unfavorable<br>5: Distinctly unfavorable |
| | (d) Aftertaste | Comparison to products without treatment with any reducing agent | 1: Distinctly preferable<br>2: Slightly preferable<br>3: Undecided<br>4: Rather unfavorable<br>5: Distinctly unfavorable |
| | (e) Odor | Comparison to products without treatment with any reducing agent | 1: Distinctly weak<br>2: Slightly weak<br>3: Comparable<br>4: Slightly sharp<br>5: Distinctly sharp |

(3) Result of Sensory Test

TABLE 18

Score distribution of the unheated test sample 6 (a product treated with reducing agent)

| | Number of panelists | | | | |
|---|---|---|---|---|---|
| | Before tasting | | When tasting | | |
| Score | (a) Coloration | (b) Odor | (c) Bitterness | (d) Aftertaste | (e) Odor |
| 1 | 4 | 3 | 0 | 3 | 4 |
| 2 | 4 | 5 | 7 | 4 | 4 |
| 3 | 0 | 0 | 1 | 1 | 0 |
| 4 | 0 | 0 | 0 | 0 | 0 |
| 5 | 0 | 0 | 0 | 0 | 0 |

TABLE 19

Score distribution of the heated test sample
6, a product treated with reducing agent

| | Number of panelists | | | | |
|---|---|---|---|---|---|
| | Before tasting | | When tasting | | |
| Score | (a) Coloration | (b) Odor | (c) Bitterness | (d) Aftertaste | (e) Odor |
| 1 | 6 | 4 | 3 | 4 | 5 |
| 2 | 2 | 3 | 4 | 1 | 1 |
| 3 | 0 | 1 | 1 | 3 | 2 |
| 4 | 0 | 0 | 0 | 0 | 0 |
| 5 | 0 | 0 | 0 | 0 | 0 |

The evaluation results in Tables 18 and 19 do not show the evaluation results of (a) coloration, (b) odor, (c) bitterness, (d) aftertaste, and (e) odor for the product without treatment with any reducing agent (the heated/unheated test sample 1) per se; however, as indicated in the evaluation standard, the evaluation results in Tables 18 and 19 were for the product treated with reducing agent evaluated based on those of the product without treatment with any reducing agent, and therefore the evaluation results of the product without treatment with any reducing agent per se correspond to the midpoint of "3" for each evaluation item, when evaluated based on the 5-point evaluation scale shown in the evaluation standard.

By contrast, as clear from the evaluation results in Table 18, the unheated test sample 6, i.e., an unheated product treated with reducing agent gave the numbers of panelists, who had judged as "1-point" as the highest score on the 5-point evaluation scale for the evaluation items of (a) coloration, (b) odor, (c) bitterness, (d) aftertaste, and (e) odor, to be four, three, zero, three, and four (14 subjects in total), respectively, each among the eight panelists. While, the heated test sample 6 shown in the evaluation results in Table 18, i.e., a heated product treated with reducing agent had the numbers of panelists, who had judged as "1-point" as the highest score in the 5-point evaluation scale for the evaluation items of (a) coloration, (b) odor, (c) bitterness, (d) aftertaste, and (e) odor, to be six, four, three, four, and five (22 subjects in total), respectively, each among the eight panelists. These results indicate that the product treated with reducing agent is a relatively high-quality glycosyl hesperetin that is effectively reduced in the odor, as well as bitterness and coloration, which are characteristics of products without treatment with any reducing agent.

Similarly, as clear from the evaluation results in Table 19, the unheated test sample 6, i.e., an unheated product treated with reducing agent gave the numbers of panelists, who had judged as "4-point" as being 1-point higher than the lowest level of 5-point upon the 5-point evaluation scale for the evaluation items of (a) coloration, (b) odor, (c) bitterness, (d) aftertaste, and (e) odor, were respectively all zero (zero in total). While, as clear from the evaluation results in Table 18, the heated test sample 6, i.e., a heated product with reducing agent gave the numbers of panelists, who had judged "4-point" as being 1-point higher than the lowest level of 5-point upon the 5-point evaluation scale for the evaluation items of (a) coloration, (b) odor, (c) bitterness, (d) aftertaste, and (e) odor, were respectively all zero (zero in total). These results show that products treated with reducing agents are relatively high-quality compositions containing glycosyl hesperetin that are effectively reduced in odor, as well as in miscellaneous tastes and coloration, compared to products without treatment with any reducing agent.

These results elucidated that, compared to products without treatment with any reducing agent, products treated with reducing agents independently of being heated or unheated are distinctly advantageous in terms of all the evaluation items of (a) coloration, (b) odor, (c) bitterness, (d) aftertaste, and (e) odor, which are characteristics of products without treatment with any reducing agent, wherein the difference in quality between the heated and unheated products becomes more distinct when they are heated.

When subjected to "(2) Sensory test" as in this Experiment 6, the test samples 5, 7, and 8 as in the above Experiment 4 gave substantially the same results as in the above test sample 6.

Thus, it was revealed that products treated with reducing agents are significantly reduced in bitterness and aftertaste, i.e., miscellaneous tastes, which are characteristics of products without treatment with any reducing agent, and they are also distinctly reduced in coloration and odor compared to those of products without treatment with any reducing agent.

The following examples explain the present invention in more detail but they should never limit the scope of the present invention.

Example 1

<External Dermal Agent for Reducing Skin Yellowness>

Similarly as in the method disclosed in Example A-2 in Japanese Patent Kokai No. 346792/99, seven parts by mass of dextrin with a dextrose equivalent (DE) of 20 was used per one part by mass of hesperidin, and the mixture was added with 20 units/g dextrin of a cyclomaltodextrin glucanotransferase derived from *Bacillus stearothermophilus*, commercialized by Hayashibara Co., Ltd., Okayama, Japan, enzymatically reacted for 24 hours while keeping the pH at 6.0 and the temperature at 75° C. to obtain a syrup composition containing glycosyl hesperetin, which was then added with "GLUCOZYME", a product name of a glucoamylase specimen, commercialized by Nagase ChemteX Corporation, Osaka, Japan, in an amount of 100 units per gram of the solids, d.s.b., of the syrup composition to effect an enzymatic reaction at 50° C. for five hours. The resulting composition containing α-glycosyl hesperetin was concentrated in vacuo and pulverized to obtain a particulate composition containing glycosyl hesperetin in a yield of about 60% to the mass, d.s.b., of the material hesperidin. The product contained 77.0% of α-glucosyl hesperidin, 15.5% of hesperidin, and 7.5% of other ingredients.

The product had a furfural content of 310 ppb, 4-VA content of 40.0 ppb, coloration degree of 0.24, and electric conductivity of about 11 μS/cm. Also, the product contained calcium, potassium, magnesium, and sodium in respective amounts of about 3 ppm, about 0.2 ppm, about 0.4 ppm, and about 1 ppm, on a dry solid basis.

When externally applied to humans intact or after processed into cosmetics, quasi-drugs, or pharmaceuticals, the product effectively reduces the already-generated skin yellowness, the reduction of which has been recognized to be difficult. The product is advantageously used safely and easily for a relatively long period of time.

Example 2

<External Dermal Agent for Reducing Skin Yellowness>

Four parts by mass of 1 N aqueous sodium hydroxide solution was heated to 80° C. and, while keeping the temperature, added with one part by mass of hesperidin and seven parts by mass of dextrin (DE 20), followed by stirring the mixture to dissolve the contents therein for 30 min, adjusting the resulting solution to pH 9.0, adding 30 units/g dextrin of a CGTase, derived from *Geobacillus stearothermophilus* Tc-91 strain (FERM BP-11273 deposited on 30 Jul. 1973) deposited for International Patent Organism Depositary in National Institute of Advanced Industrial Science and Technology, Tsukuba Central 6, 1-1, Higashi 1-chome, Tsukuba-shi, Ibaraki-ken, 305-8566 Japan, and enzymatically reacting the mixture at pH 6.9 and 50° C. for 18 hours to convert about 70% of hesperidin into α-glycosyl hesperidin. Thereafter, the resulting enzymatic reaction solution was added with sodium pyrosulfite as a reducing agent in an amount of 0.05% by mass to the solution, heated at 100° C. for 30 min to inactivate the remaining enzymes, added with 100 units/g solids, d.s.b., of the enzymatic reaction solution of "GLUCOZYME", a product name of a glucoamylase specimen, commercialized by Nagase ChemteX Corporation, Osaka, Japan, and enzymatically reacted for five hours while keeping the pH at 5.0 and the temperature at 55° C. to form α-glucosyl hesperidin. The resulting enzymatic reaction solution was heated to inactivate the remaining enzyme and filtered, followed by feeding the resulting filtrate to a column packed with "DIAION HP-10", a product name of a porous synthetic adsorbent, commercialized by Mitsubishi Chemical Corporation, Tokyo, Japan, at a space velocity (SV) of 2. As a result, α-glucosyl hesperidin and intact hesperidin in the solution adsorbed on the porous synthetic adsorbent, but the remaining D-glucose, salts, and the like were eluted out from the column without adsorption. Thereafter, the column was fed with refined water for washing and further fed with an aqueous ethanol solution while increasing stepwisely the concentration of ethanol to collect fractions containing α-glucosyl hesperidin, followed by pooling the fractions, concentrating the pooled fractions in vacuo, and pulverizing the concentrate to obtain a pale yellow particulate composition containing glycosyl hesperetin in a yield of about 70% to the mass, d.s.b., of the material hesperidin. The resulting particulate composition containing glycosyl hesperetin contained 80.0% of α-glucosyl hesperidin, 12.3% of hesperidin, and 7.7% of other ingredients.

The product had a furfural content of 12 ppb, 4-VA content of 2 ppb, coloration degree of 0.19, and electric conductivity of about 6 μS/cm. Also, the product contained calcium, potassium, magnesium, and sodium in respective amounts of about 0.4 ppm, about 0.05 ppm, about 0.1 ppm, and about 0.1 ppm, on a dry solid basis.

Compared to the particulate composition containing glycosyl hesperetin obtained in Example 1 without using any prescribed reducing agent, the above product has advantageously characteristic features in that it is significantly reduced in miscellaneous tastes and coloration and distinctly reduced in odor, wherein the odor as well as miscellaneous-tastes/coloration are effectively reduced even when heated for 30 min under a relatively high temperature condition of 90 to 100° C.

When externally used alone or after processed into cosmetics, quasi-drugs, or pharmaceuticals, the product effectively reduces the already-generated skin yellowness that has been considered difficult to attain. The product has an advantageous merit in that it can be used safely and easily for a relatively long period of time. Even when kept or stored at a temperature within the above temperature range or a lower temperature thereof for several tens of minutes to several months, the product exerts an advantageous effect and function of being effectively reduced in the miscellaneous tastes and coloration, as well as odor, which are inherent thereto.

Example 3

<External Dermal Agent for Reducing Skin Yellowness>

Four parts by mass of 1 N aqueous sodium hydroxide solution was heated to 80° C. and, while keeping the temperature, successively added with one part by mass of hesperidin, four parts by mass of dextrin (DE 10), and 0.06 part by mass of sodium sulfite, followed by dissolving the contents in the mixture while stirring for 30 min, neutralizing the resulting solution with 0.01 N hydrochloric acid solution, promptly adding 20 units/g dextrin of a CGTase derived from *Geobacillus stearothermophilus* Tc-91 strain (FERM BP-11273) deposited for International Patent Organism Depositary in National Institute of Advanced Industrial Science and Technology, Tsukuba Central 6, 1-1, Higashi 1-chome, Tsukuba-shi, Ibaraki-ken, 305-8566 Japan, and keeping the mixture at pH 6.0 and 75° C. for 24 hours under stirring conditions to effect an enzymatic reaction. The resulting enzymatic reaction solution was sampled and analyzed on high-performance liquid chromatography (HPLC), revealing that about 69% of hesperidin was converted to α-glycosyl hesperidin. To the obtained enzymatic reaction solution was added 0.03% by mass of sodium pyrosulfite, heated at 90° C. for 120 min, added with "GLUCOZYME", a product name of a glucoamylase specimen, commercialized by Nagase ChemteX Corporation, Osaka, Japan, in an amount of 50 units per gram of α-glycosyl hesperidin, d.s.b., as an intermediate product, and reacted for 10 hours while keeping the pH at 5.0 and the temperature at 55° C. to form α-glucosyl hesperidin. The resulting enzymatic reaction solution was heated to inactivate the remaining enzymes and filtered, followed by feeding the resulting filtrate to a column packed with "DIAION HP-10", a product name of a porous synthetic adsorbent, commercialized by Mitsubishi Chemical Corporation, Tokyo, Japan, at SV 2. As a result, α-glucosyl hesperidin and intact hesperidin in the solution adsorbed on the porous synthetic adsorbent, but the remaining saccharides, salts, and the like were eluted out from the column without adsorption. Thereafter, the column was fed with refined water for washing and further fed with an aqueous ethanol solution while increasing stepwisely the concentration of ethanol to collect fractions containing α-glucosyl hesperidin, followed by pooling the fractions, concentrating the pooled fractions in vacuo, and pulverizing the concentrate to obtain a pale yellow particulate composition containing glycosyl hesperetin in a yield of about 68% to the mass, d.s.b., of the material hesperidin. The particulate composition containing glycosyl hesperetin, obtained in this example, contained 79.0% of α-glucosylhesperidin, 14.0% of hesperidin, and 7.0% of other ingredients.

The product had a furfural content of 11 ppb, 4-VA content of 1.5 ppb, coloration degree of 0.14, and electric conductivity of about 4 μS/cm. Also, the product contained calcium, potassium, magnesium, and sodium in respective amounts of about 0.4 ppm, about 0.06 ppm, about 0.1 ppm, and about 0.1 ppm, on a dry solid basis.

Compared to the particulate composition containing glycosyl hesperetin obtained in Example 1 without using any prescribed reducing agent, the above product has advantageously characteristic features: The product is significantly reduced in miscellaneous tastes and coloration and distinctly reduced in odor, and it is also effectively reduced in odor as well as miscellaneous-tastes/coloration even when heated for 30 min under a relatively high temperature condition of 90 to 100° C.

When externally used alone or after processed into cosmetics, quasi-drugs, or pharmaceuticals, the product effectively reduces the already-generated skin yellowness that has been considered difficult to attain. The product has an advantageous merit in that it can be used safely and easily for a relatively long period of time. Even when kept or stored at a temperature within the above temperature range or a lower temperature thereof for several tens of minutes to several months, the product exerts an advantageous effect and function of being effectively reduced in the miscellaneous tastes and coloration, as well as odor, which are inherent thereto.

Example 4

<External Dermal Agent for Reducing Skin Yellowness>

Four parts by mass of 1 N aqueous sodium hydroxide solution was heated to 80° C. and, while keeping the temperature, successively added with 0.1 part by mass of sodium sulfite as a reducing agent, one part by mass of hesperidin, and four parts by mass of dextrin (DE10), followed by dissolving the contents in the mixture while stirring for 30 min, neutralizing the resulting solution with 0.01 N hydrochloric acid solution, promptly adding 20 units/g dextrin, d.s.b., of a CGTase, derived from *Geobacillus stearothermophilus* Tc-91 strain (FERM BP-11273) deposited for International Patent Organism Depositary in National Institute of Advanced Industrial Science and Technology, Tsukuba Central 6, 1-1, Higashi 1-chome, Tsukuba-shi, Ibaraki-ken, 305-8566 Japan, and keeping the mixture at pH 6.0 and 75° C. for 24 hours under stirring conditions to effect an enzymatic reaction. Thus, about 72% of hesperidin was converted to α-glcosyl hesperidin. The enzymatic reaction solution thus obtained was heated to inactivate the remaining enzyme and filtered, followed by feeding the resulting filtrate to a column packed with "DIAION HP-20", a product name of a porous synthetic adsorbent, commercialized by Mitsubishi Chemical Corporation, Tokyo, Japan, at SV 2. As a result, α-glycosyl hesperidin and intact hesperidin in the solution were adsorbed on the porous synthetic adsorbent, but the remaining D-glucose, salts, and the like were eluted out from the column without adsorption. Thereafter, the column was fed with refined water for washing and further fed with an aqueous ethanol solution while increasing stepwise the concentration of ethanol to collect fractions containing α-glycosyl hesperidin, followed by pooling the fractions, concentrating the pooled fractions in vacuo, and pulverizing the concentrate to obtain a pale yellow particulate composition containing α-glycosyl hesperidin in a yield of about 71% to the mass, d.s.b., of the material hesperidin. The particulate composition containing glycosyl hesperetin obtained in this example contained 76.0% of α-glycosyl hesperidin, 18.5% of hesperidin, and 5.5% of other ingredients.

The product had a furfural content of 10 ppb, 4-VA content of 3.0 ppb, coloration degree of 0.17, and electric conductivity of about 4 µS/cm. Also, the product contained calcium, potassium, magnesium, and sodium in respective amounts of about 0.3 ppm, about 0.04 ppm, about 0.1 ppm, and about 0.05 ppm, on a dry solid basis.

Compared to the particulate composition containing glycosyl hesperetin obtained in Example 1 without using any prescribed reducing agent, the above product has advantageously characteristic features: The product is significantly reduced in miscellaneous tastes and coloration and distinctly reduced in odor, and it is also effectively reduced in odor as well as miscellaneous tastes and coloration even when heated for 30 min under a relatively high temperature condition of 90 to 100° C.

When externally used alone or after processed into cosmetics, quasi-drugs, or pharmaceuticals, the product effectively reduces the already-generated skin yellowness that has been considered difficult to attain. The product has an advantageous merit in that it can be used safely and easily for a relatively long period of time. Even when kept or stored at a temperature within the above temperature range or a lower temperature thereof for several tens of minutes to several months, the product exerts an advantageous effect and function of being effectively reduced in the miscellaneous tastes and coloration, as well as odor, which are inherent thereto.

Example 5

<External Dermal Agent for Reducing Skin Yellowness>

One part by mass of hesperidin, 10 parts by mass of dextrin (DE 8), and 0.05 part by mass of sodium pyrosulfite as a reducing agent were added to 500 parts by mass of water. The mixture was heated at pH 9.5 and 90° C. for 70 min, added with 30 units/g dextrin, d.s.b., of a CGTase, derived from *Geobacillus stearothermophilus* Tc-91 strain (FERM BP-11273) deposited for International Patent Organism Depositary in National Institute of Advanced Industrial Science and Technology, Tsukuba Central 6, 1-1, Higashi 1-chome, Tsukuba-shi, Ibaraki-ken, 305-8566 Japan, kept for 40 hours while keeping the pH at 8.2 and the temperature at 65° C. under stirring conditions, added with 0.05 part by mass of sodium pyrosulfite as a reducing agent to the enzymatic reaction solution just before the completion of the enzymatic reaction, heated at 85° C. to inactivate the remaining enzyme, added with 100 units/g solids, d.s.b., of the solution of "GLUCOZYME", a product name of a glucoamylase specimen, commercialized by Nagase ChemteX Corporation, Osaka, Japan, and reacted for five hours while keeping the pH at 5.0 and the temperature at 55° C. to form α-glucosyl hesperidin. The enzymatic reaction solution thus obtained was heated to inactive the remaining enzymes. The resulting enzymatic reaction solution was added with 0.5 part by mass of "SOLUBLE HESPERIDINASE <Tanabe> No. 2", a product name of a hesperidinase specimen, commercialized by Mitsubishi Tanabe Pharma Corporation, Osaka, Japan, adjusted to pH 4, and enzymatically reacted at 55° C. for 24 hours. The resulting enzymatic reaction solution was added with 0.01 part by mass of sodium pyrosulfite, heated to inactivate the remaining enzyme, and filtered, followed by feeding the filtrate to a column packed with "DIAION HP-10", a product name of a porous synthetic adsorbent, commercialized by Mitsubishi Chemical Corporation, Tokyo, Japan, at SV 2. As a result, α-glucosylhesperidin, 7-O-β-glucosyl hesperetin, and intact hesperidin in the solution were adsorbed on the porous synthetic adsorbent, but the remaining D-glucose, salts, and the like were eluted out from the column without adsorption. Thereafter, the column was fed with refined water for washing and further fed with an aqueous ethanol solution while increasing stepwise the concentration of ethanol to collect fractions containing α-glycosyl hesperidin, followed by pooling the fractions, concentrating the pooled fractions in vacuo, and pulverizing the concentrate to obtain a pale yellow particulate composition containing glycosyl hesperetin in a yield of about 70% to the mass, d.s.b., of the material hesperidin. The particulate composition containing glycosyl hesperetin obtained in this example contained 81.9% of α-glucosylhesperidin, 0.5% of hesperidin, 8.9% of 7-O-β-glucosyl hesperetin, and 8.7% of other ingredients.

The product had a furfural content of 9 ppb, 4-VA content of 2.0 ppb, coloration degree of 0.16, and electric conductivity of about 4 μS/cm. Also, the product contained calcium, potassium, magnesium, and sodium in respective amounts of about 0.3 ppm, about 0.03 ppm, about 0.05 ppm, and about 0.05 ppm, on a dry solid basis.

Compared to the particulate composition containing glycosyl hesperetin obtained in Example 1 without using any prescribed reducing agent, the above product has advantageously characteristic features: The product is significantly reduced in miscellaneous tastes and coloration and distinctly reduced in odor, and it is also effectively reduced in odor as well as miscellaneous tastes and coloration even when heated for 30 min under a relatively high temperature condition of 90 to 100° C.

When externally used alone or after processed into cosmetics, quasi-drugs, or pharmaceuticals, the product effectively reduces the already-generated skin yellowness that has been considered difficult to attain. The product has an advantageous merit in that it can be used safely and easily for a relatively long period of time. Even when kept or stored at a temperature within the above temperature range or a lower temperature thereof for several tens of minutes to several months, the product exerts an advantageous effect and function of being effectively reduced in the miscellaneous tastes and coloration, as well as odor, which are inherent thereto.

Example 6

<External Dermal Agent for Reducing Skin Yellowness>

Fifty parts by mass of hesperidin and one part by mass of sodium hyposulfite were dissolved by heating at 80° C. in 0.9 part by mass of 0.25 N aqueous sodium hydroxide solution. One hundred fifty parts by mass of a dextrin with DE 8 was added to and dissolved in the above solution, followed by adjusting the resulting solution to pH 9.0, adding to the solution 15 units per one part by mass of dextrin of a CGTase, derived from *Geobacillus stearothermophilus* Tc-91 strain (FERM BP-11273) deposited for International Patent Organism Depositary in National Institute of Advanced Industrial Science and Technology, Tsukuba Central 6, 1-1, Higashi 1-chome, Tsukuba-shi, Ibaraki-ken, 305-8566 Japan, adjusting the mixture to pH 8.3 while heating it up to 60° C., and subjecting the resulting mixture to an enzymatic reaction for six hours. Thereafter, the enzymatic reaction mixture was adjusted to pH 7.0, heated to 68° C., and then enzymatically reacted for 40 hours. After completion of the enzymatic reaction, the resulting enzymatic reaction mixture was heated to inactivate the remaining enzyme and filtered to obtain an enzymatic reaction solution. An HPLC analysis of the enzymatic reaction solution revealed that 72% of hesperidin in the solution before the enzymatic reaction was converted to α-glucosyl hesperidin and the remaining 28% of hesperidin still remained intact. The enzymatic reaction solution was admixed with two parts by mass of "Soluble hesperidinase <TANABE> 2", a product name of a hesperidinase specimen as α-L-rhamnosidase, commercialized by Tanabe Seiyaku Co., Ltd., Tokyo, Japan, adjusted to pH 4, enzymatically reacted at 55° C. for 24 hours, added with one part by mass of "GLUCO-ZYME", a product name of a glucoamylase specimen, commercialized by Nagase ChemteX Corporation, Osaka, Japan, and further enzymatically reacted at 55° C. for 24 hours. After completion of the enzymatic reaction, the resulting enzymatic reaction solution was heated to inactivate the remaining enzymes, fed to a column packed with "AMBERLITE XAD-7", a product name of a porous adsorbing resin with a medium polarity, commercialized by Rohm & Hass Company, Philadelphia, USA., followed by washing the column with water, and eluting out ingredients adsorbed on the resin with 80 v/v % aqueous ethanol solution. After removing ethanol in the eluate, the resulting eluate was freeze dried to obtain a particulate composition containing glycosyl hesperetin with 82.0% of α-glucosyl hesperidin, 8.0% of 7-O-β-glucosyl hesperetin, 1.0% of hesperidin, and 9.0% of other ingredients.

The product had a furfural content of 10 ppb, 4-VA content of 1.5 ppb, coloration degree of 0.15, and electric conductivity of less than 10 μS/cm. Also, the product contained calcium, potassium, magnesium, and sodium in respective amounts of about 0.4 ppm, about 0.04 ppm, about 0.1 ppm, and about 0.2 ppm, on a dry solid basis.

Compared to the particulate composition containing glycosyl hesperetin obtained in Example 1 without using any prescribed reducing agent, the above product has advantageously characteristic features: It is significantly reduced in miscellaneous tastes and coloration and distinctly reduced in odor, and it is also effectively reduced in odor as well as miscellaneous tastes and coloration even when heated for 30 min under a relatively high temperature condition of 90 to 100° C.

When externally used alone or after processed into cosmetics, quasi-drugs, or pharmaceuticals, the product effectively reduces the already-generated skin yellowness that has been considered difficult to attain. The product has an advantageous merit in that it can be used safely and easily for a relatively long period of time. Even when kept or stored at a temperature within the above temperature range or a lower temperature thereof for several tens of minutes to several months, the product exerts an advantageous effect and function of being effectively reduced in the miscellaneous tastes and coloration, as well as odor, which are inherent thereto.

Example 7

<External Dermal Agent for Reducing Skin Yellowness>

A pale yellow particulate composition containing glycosyl hesperetin was obtained similarly as in Example 1, except for adding 0.001% of potassium pyrosulfite as a reducing agent to an enzymatic reaction solution, in a yield of about 69% to the mass, d.s.b., of the material hesperidin. The particulate composition containing glycosyl hesperetin obtained in this example contained 79.5% of α-glucosyl hesperidin, 13.8% of hesperidin, and 6.7% of other ingredients.

The product had a furfural content of 180 ppb, 4-VA content of 20.0 ppb, coloration degree of 0.23, and electric conductivity of less than 10 μS/cm. Also, the product contained calcium, potassium, magnesium, and sodium in respective amounts of about 0.5 ppm, about 0.08 ppm, about 0.1 ppm, and about 0.3 ppm, on a dry solid basis.

Although the product is rather inferior to the particulate compositions containing glycosyl hesperetin obtained in Examples 2 to 5, the product is, compared to products without treatment with any reducing agent, distinctly reduced in coloration and odor and significantly reduced in miscellaneous tastes; and it is also effectively reduced in coloration and odor as well as miscellaneous tastes even after heated for 30 min under a relatively high temperature condition of 90 to 100° C., compared to products without treatment with any reducing agent.

When externally used alone or after processed into cosmetics, quasi-drugs, or pharmaceuticals, the product effectively reduces the already-generated skin yellowness that has been considered difficult to attain. The product has an advantageous merit in that it can be used safely and easily for a relatively long period of time. Even when kept or stored at a temperature within the above temperature range or a lower temperature thereof for several tens of minutes to several months, the product exerts an advantageous effect and function of being effectively reduced in the miscellaneous tastes and coloration, as well as odor, which are inherent thereto.

Example 8

<External Dermal Agent for Reducing Skin Yellowness>

A pale yellow particulate composition containing glycosyl hesperetin was obtained similarly as in Example 7, except for replacing the potassium pyrosulfite with sodium hydrogen sulfite, in a yield of about 65% to the mass, d.s.b., of the material hesperidin. The particulate composition obtained in this example contained 77.2% of α-glucosyl hesperidin, 16.5% of hesperidin, and 6.3% of other ingredients.

The product had a furfural content of 191 ppb, 4-VA content of 28.7 ppb, coloration degree of 0.23, and electric conductivity of less than 10 μS/cm. Also, the product contained calcium, potassium, magnesium, and sodium in respective amounts of about 0.5 ppm, about 0.07 ppm, about 0.09 ppm, and about 0.4 ppm, on a dry solid basis.

Although the product is rather inferior to the particulate compositions containing glycosyl hesperetin obtained in Examples 2 to 6, the product is, compared to products without treatment with any reducing agent, distinctly reduced in coloration and odor and significantly reduced in miscellaneous tastes; and it is also effectively reduced in coloration and odor as well as miscellaneous tastes even after heated for 30 min under a relatively high temperature condition of 90 to 100° C., compared to products without treatment with any reducing agent.

When externally used alone or after processed into cosmetics, quasi-drugs, or pharmaceuticals, the product effectively reduces the already-generated skin yellowness that has been considered difficult to attain. The product has an advantageous merit in that it can be used safely and easily for a relatively long period of time. Even when kept or stored at a temperature within the above temperature range or a lower temperature thereof for several tens of minutes to several months, the product exerts an advantageous effect and function of being effectively reduced in the miscellaneous tastes and coloration, as well as odor, which are inherent thereto.

Example 9

<External Dermal Agent for Reducing Skin Yellowness>

One part by mass of anyone of the seven types of particulate external dermal agents for reducing skin yellowness obtained in Examples 2 to 8, 0.001 part by mass of anthocyanin, 30 parts by mass of refined water, and an adequate amount of a pH-controlling agent, and the mixture was stirred, adjusted to pH 7.0, microfiltered, and antiseptically injected into sterilized containers to obtain seven types of external dermal agents for reducing skin yellowness in a liquid form according to the present invention.

The products substantially free of coloration and odor are applied externally to humans daily, successively, and easily without unpleasant feeling. When externally applied to the skin daily at a dose of about 0.01 to about 0.05 mL/cm$^2$, the products effectively exert an action of reducing the already-generated skin yellowness.

Example 10

<External Dermal Agent for Reducing Skin Yellowness>

To 50 parts by mass of refined water were added 0.01 part by mass of any one of the pulverized compositions containing glycosyl hesperetin obtained in Examples 2 to 8 and 0.0001 part by mass of hesperetin, and the mixture was mixed to homogeneity, sterilized by heating, and antiseptically injected into sterilized containers to obtain seven types of external dermal agents for reducing skin yellowness.

All the products are substantially free of coloration and odor and they can be used daily, successively, and easily without unfavorable feeling. When externally applied daily to the skin at a dose of about 0.01 to about 0.05 mL/cm$^2$, the products effectively exert an action of reducing the already-generated skin yellowness.

Example 11

<External Dermal Agent for Reducing Skin Yellowness>

To one part by mass of the pulverized composition containing glycosyl hesperetin, which had been prepared in Example 1 without using any of the prescribed reducing agents, were added one or more reducing agents selected from sodium sulfite, sodium hyposulfite, potassium pyrosulfite, sodium pyrosulfite, and sulfur dioxide in a total amount of 0.0005 part by mass. The resulting mixture was homogeneously dissolved in 50 parts by mass of refined water, microfiltered, and antiseptically injected into sterilized containers to obtain external dermal agents for reducing skin yellowness in a liquid form.

These products are advantageous in storage stability and thermostability without any substantial increment or change in miscellaneous-tastes/coloration, and odor, which are all derivable therefrom, even after stored for several tens of minutes to several months under an ambient temperature or a relatively high temperature condition.

The products are substantially free of coloration and odor and externally applied to humans daily, successively, and easily without unfavorable feeling. When applied to the skin at a dose of about 0.01 to about 0.05 mL/cm$^2$, the products effectively exert an action of reducing the already-generated skin yellowness.

Example 12

<External Dermal Agent for Reducing Skin Yellowness>

Eight types of external dermal agents for reducing skin yellowness in a spray type were produced by mixing the following ingredients, which fulfill the criteria of Japanese Standards of Cosmetic Ingredients or Japanese Cosmetic Ingredients Codex (JCIC), in a usual manner according to the following composition ratio:

<Composition Ratio>

| | |
|---|---|
| A pulverized composition containing glycosyl hesperetin obtained in any one of Examples 1 to 8. | 0.1 part by mass |
| Sodium hyaluronate solution (1%, JCIC) | 15 parts by mass |
| Trehalose (JCIC) | 0.5 part by mass |
| L-cystine (JCIC) | 0.05 part by mass |
| *Salvia Officinalis*(Sage) extract (JCIC) | 1.0 part by mass |
| Peach (*Prunus Persica*) Leaf Extract (JCIC) | 0.5 part by mass |
| Polyoxyethylene (20) polyoxypropylene (8) cetyl ether (JCIC) | 0.3 part by mass |
| Refined water (JCIC) | q.s. |
| Total | 100 parts by mass |

The product was injected into a 100-mL spray container to obtain a liquid spray. When applied to a prescribed part of the skin to be reduced in skin yellowness in an effective amount at a frequency of one to five times a day everyday or every other day over several days to several months, the product effectively reduces the already-generated skin yellowness, has a superior moisture-permeability to the skin, has an improved moisture retainability, and has a useful refreshing feeling of use. The product has a mild cleaning action and it is useful as a low-stimulus spray for cleaning.

INDUSTRIAL APPLICABILITY

The external dermal agent for reducing skin yellowness of the present invention effectively reduces the already-generated skin yellowness. In particular, examples of glycosyl hesperetins for use in the external dermal agent for reducing skin yellowness according to the present invention, the glycosyl hesperetins prepared by using the prescribed reducing agents can be used by humans daily, successively, safely, and easily without inducing unfavorable feeling, because they are distinctly reduced in coloration and unfavorable odor compared to conventional glycosyl hesperetins prepared without using any of the prescribed reducing agents. Thus, the present invention has such a magnificent impact on the art and has an industrial applicability to the art.

The invention claimed is:

1. A method for reducing skin yellowness and carbonyl protein already generated in the skin of a subject in need thereof, which comprises a step of applying an external dermal agent comprising hesperetin and/or glycosyl hesperetin along with one or more members selected from the group consisting of maltose, maltotetraose, glycosyl trehalose, lactic acid, ferulic acid, glucuronic acid, acetic acid, sorbic acid, and sodium glutamate as effective ingredients to the skin of said subject, wherein a ratio of carbonyl protein to no test agent control is measured and is reduced after applying the external dermal agent.

2. The method of claim 1, wherein said glycosyl hesperetin is one or more members selected from the group consisting of hesperidin, α-glycosyl hesperidin, and 7-O-β-glucosyl hesperetin.

3. The method of claim 2, wherein said α-glycosyl hesperidin is α-glucosyl hesperidin.

4. The method of claim 1, wherein said glycosyl hesperetin contains glycosyl hesperetin in an amount of at least 50% by mass but less than 100% by mass, on a dry solid basis.

5. The method of claim 2, wherein the purity of said α-glycosyl hesperidin in said glycosyl hesperetin is at least 50% by mass but less than 100% by mass, on a dry solid basis.

6. The method of claim 1, wherein said external dermal agent further comprises one or more other members selected from the group consisting of saccharides, organic acids, and amino acids.

7. The method of claim 1, wherein said external dermal agent contains said hesperetin and/or said glycosyl hesperetin in a total amount of at least 0.0001% by mass but less than 100% by mass.

8. The method of claim 1, wherein said external dermal agent is in the form of a tablet, granule, powder, spray, suspension, paste, jelly, or liquid.

* * * * *